United States Patent
Josse et al.

[11] Patent Number: 5,852,229
[45] Date of Patent: Dec. 22, 1998

[54] PIEZOELECTRIC RESONATOR CHEMICAL SENSING DEVICE

[75] Inventors: Fabien J. Josse, Milwaukee, Wis.; Dennis S. Everhart, Alpharetta, Ga.

[73] Assignee: Kimberly-Clark Worldwide, Inc., Neenah, Wis.

[21] Appl. No.: 654,993

[22] Filed: May 29, 1996

[51] Int. Cl.⁶ .................................................. G01N 27/00
[52] U.S. Cl. .................... 73/24.06; 73/61.49; 73/61.79; 310/365
[58] Field of Search ................................ 73/24.01, 24.06, 73/32 A, 61.45, 61.49, 61.79, 64.53; 310/340, 367, 369, 365

[56] References Cited

U.S. PATENT DOCUMENTS

| | | | |
|---|---|---|---|
| 4,312,228 | 1/1982 | Wohltjen | 73/597 |
| 4,399,686 | 8/1983 | Kindlund et al. | 73/24.06 |
| 4,561,286 | 12/1985 | Sekler et al. | 73/24.06 |
| 4,596,697 | 6/1986 | Ballato . | |
| 4,690,715 | 9/1987 | Allara et al. . | |
| 4,844,613 | 7/1989 | Batchelder et al. . | |
| 4,877,747 | 10/1989 | Stewart . | |
| 4,895,017 | 1/1990 | Pyke et al. | 73/24.06 |
| 4,992,385 | 2/1991 | Godfrey . | |
| 5,023,053 | 6/1991 | Finlan . | |
| 5,035,863 | 7/1991 | Finlan et al. . | |
| 5,055,265 | 10/1991 | Finlan . | |
| 5,064,619 | 11/1991 | Finlan . | |
| 5,076,094 | 12/1991 | Frye et al. | 73/24.06 |
| 5,182,135 | 1/1993 | Giesecke et al. . | |
| 5,189,902 | 3/1993 | Groeninger . | |
| 5,235,238 | 8/1993 | Nomura et al. . | |
| 5,242,828 | 9/1993 | Bergstrom et al. . | |
| 5,327,225 | 7/1994 | Bender et al. . | |
| 5,334,303 | 8/1994 | Muramatsu et al. . | |
| 5,374,563 | 12/1994 | Maule . | |
| 5,402,075 | 3/1995 | Lu et al. . | |
| 5,404,756 | 4/1995 | Briggs et al. . | |
| 5,415,842 | 5/1995 | Maule . | |
| 5,436,161 | 7/1995 | Bergstrom et al. . | |
| 5,455,475 | 10/1995 | Josse et al. . | |
| 5,512,131 | 4/1996 | Kumar et al. . | |
| 5,527,711 | 6/1996 | Tom-Moy et al. | 436/518 |

FOREIGN PATENT DOCUMENTS

| | | |
|---|---|---|
| 0 453 820 | 10/1991 | European Pat. Off. . |
| 0 657 737 | 6/1995 | European Pat. Off. . |
| 91/05999 | 5/1991 | WIPO . |
| 96/26435 | 8/1996 | WIPO . |

OTHER PUBLICATIONS

Kumar et al., "Patterning Self–Assembled Monolayers: Applications in Material Science," *Langmuir*, vol. 10, pp. 1498–1506 (1994).

Shana et al., "Quartz Crystals Resonators as Sensors in Liquids Using the Acoustoelectric Effects," *Anal. Chem.*, vol. 66, pp. 1955–1964 (1994).

Shana et al., "Analysis of electrical equivalent circuit of quartz crystal resonator loaded with viscous conductive liquids," *J. Electroanalytical Chemistry*, vol. 379, pp. 21–33 (1994).

Mrksich et al., "Patterning self–assembled monolayers using microcontact printing: a new technology for biosensors?" *Tibtech*, vol.13, pp. 228–235 (1995).

(List continued on next page.)

*Primary Examiner*—Michael Brock
*Attorney, Agent, or Firm*—Jones & Askew

[57] ABSTRACT

The present invention comprises a sensor for measuring an analyte in a medium comprising a piezoelectric resonator having a first side with an electroded region and a second opposing side having an electroded region that is different in size and/or shape of the first electrode. The piezoelectric resonator of the present invention is capable of measuring more than one parameter thereby providing a multi-information sensing device. The present invention also includes an apparatus and method for detecting and measuring an analyte in a medium which utilizes the piezoelectric resonator sensor of the present invention.

29 Claims, 11 Drawing Sheets

OTHER PUBLICATIONS

Liedberg et al., "Molecular Gradients of ∞–Substituted Alkanethiols on Gold: Preparation and Characterization," *Langmuir*, vol. 11, pp. 3821–3827 (1995).

Kelkar et al., "Acoustic Plate Waves for Measurements of Electrical Properties of Liquids," *Microchemical Journal*, vol. 43, pp. 155–164 (1991).

Dahint et al., "Probing of strong and weak electrolytes with acoustic wave fields," *Sensors and Acuators B.*, vol. 9, pp. 155–162 (1992).

Josse et al., "On the use of ZX–LiNbO3 acoustic plate mode devices as dectectors for dilute electrolytes," *Sensors and Acuators B.*, vol. 9, pp. 97–112 (1992).

Josse et al., "Electrical Surface Perturbation of a Piezoelectric Acoustic Plate Mode by a Conductive Liquid Loading," *IEEE Transactions on Ultrasonics, Ferroelectrics and Frequency Control*, vol. 39 (4), pp. 512–518 (1992).

Kumar et al., "Features of gold having micrometer to centimeter dimensions can be formed through a combination of stamping with a elastomeric stamp and an alkanethiol 'ink' followed by chemical etching," *Appl. Phys. Lett.*, vol. 63 (14), pp. 2002–2004 (1993).

Tsai et al., "Comment on the Prediction of Segregation to Alloy Surfaces", Journal of Catalysis—Letters to the Editor, vol. 50, pp. 200–202 (1977).

Burton et al. "Prediction of Segregation to Alloy Surfaces from Bulk Phase Diagram", Phys. Rev. Letter, vol. 37, No. 21, pp. 1433–1436 (Nov. 22, 1976).

Johnson et al. "Orientation dependence of surface segregation in a dilute Ni–Au alloy", J. Vac. Sci. Technol., vol. 15, No. 2, pp. 467–469 (Mar./Apr. 1978).

Osada et al., "Intelligent Gels", Scientific American, pp. 82–87 (May 1993).

Saito et al., "Volume Phase Transition of N–Alkylacrylamide Gels", Advances on Polymer Science, vol. 109, pp. 207–232 (1993).

Okano, T. "Molecular Design of Temperature–Responsive Polymers as Intelligent Materials", Advances in Polymer Science, vol. 110, pp. 179–197 (1993).

Shibayama et al., "Volume Phase Transition and Related Phenomena of Polymer Gels", Advances in Polymer Science, vol. 109, pp. 1–62 (1993).

Kokufuta, E. "Novel Applications for Stimulus–Sensitive Polymer Gels in the Preparation of Functional Immobilized Biocatalysts", Advances in Polymer Science, vol. 110, pp. 157–177 (1993).

Osada et al, "Stimuli–Responsive Polymer Gels and Their Application to Chemomechanical Systems", Prog. Polym. Sci., vol. 18, pp. 187–226 (1993).

Irie, M. "Stimuli–Responsive Poly(N–isopropylacrylamide) Photo–and Chemical–Induced Phase Transitions", Advances in Polymer Science, vol. 110, pp. 49–65 (1993).

Abbott et al., Using Micromachining, Molecular Self–Assembly, and Wet Etching to Fabricate 0.1–1 μm–Scale Structures of Gold and Silicon, Chemistry of Materials, 6, No. 5, pp. 596–602 (1994).

Jeon et al., "Patterned Self–Assembled Monolayers Formed by Microcontact Printing Direct Selective Metalization by Chemical Vapor Deposition on Planar and Nonplanar Substrates", Langmuir, vol. 11, No. 8, pp. 3024–3026 (1995).

Kim et al., "Combining Patterned Self–Assembled Monolayers of Alkanethiolates on Gold with Anisotropic Etching of Silicon to Generate Controlled Surface Morphologies", J. Electrochem. Soc., vol. 142, No. 2, pp. 628–633 (Feb. 1995).

Folkers et al., "Self–Assembled Monolayers of Long–Chain Hydroxamic Acids on the Native Oxides of Metals", Langmuire, vol. 11, No. 3, pp. 813–824 (1995).

Kumar et al., "Patterned Condensation Figures as Optical Diffraction Gratings", Science, vol. 263, pp. 60–62 (Jan. 7, 1994).

Wilbur et al., "Microfabrication by Microcontact Printing of Self–Assembled Monolayers", Adv. Mater., vol. 6, No. 7/8, pp. 600–604 (1994).

Seah, M.P. "Quantitative Prediction of Surface Segregation", Journal of Catalysis, vol. 57, pp. 450–457 (1979).

Copy of Search Report for PCT/US97/08522 dated Aug. 8, 1997.

"Mechanical resonance gas sensors with piezoelectric excitation and detection using PVDF polymer foils" by R. Block et al., Sensors and Actuators, vol. B7, Mar. 1992, pp. 596–601.

"Sensing liquid properties with thickness–shear mode resonators" by S. J. Martin, Sensors and Actuators A, vol. A44, Sep. 1994, pp. 209–218.

Abstract of EP 0 453 820 dated Oct. 30, 1991.

Abstract of WO 96/26435 dated Aug. 29, 1996.

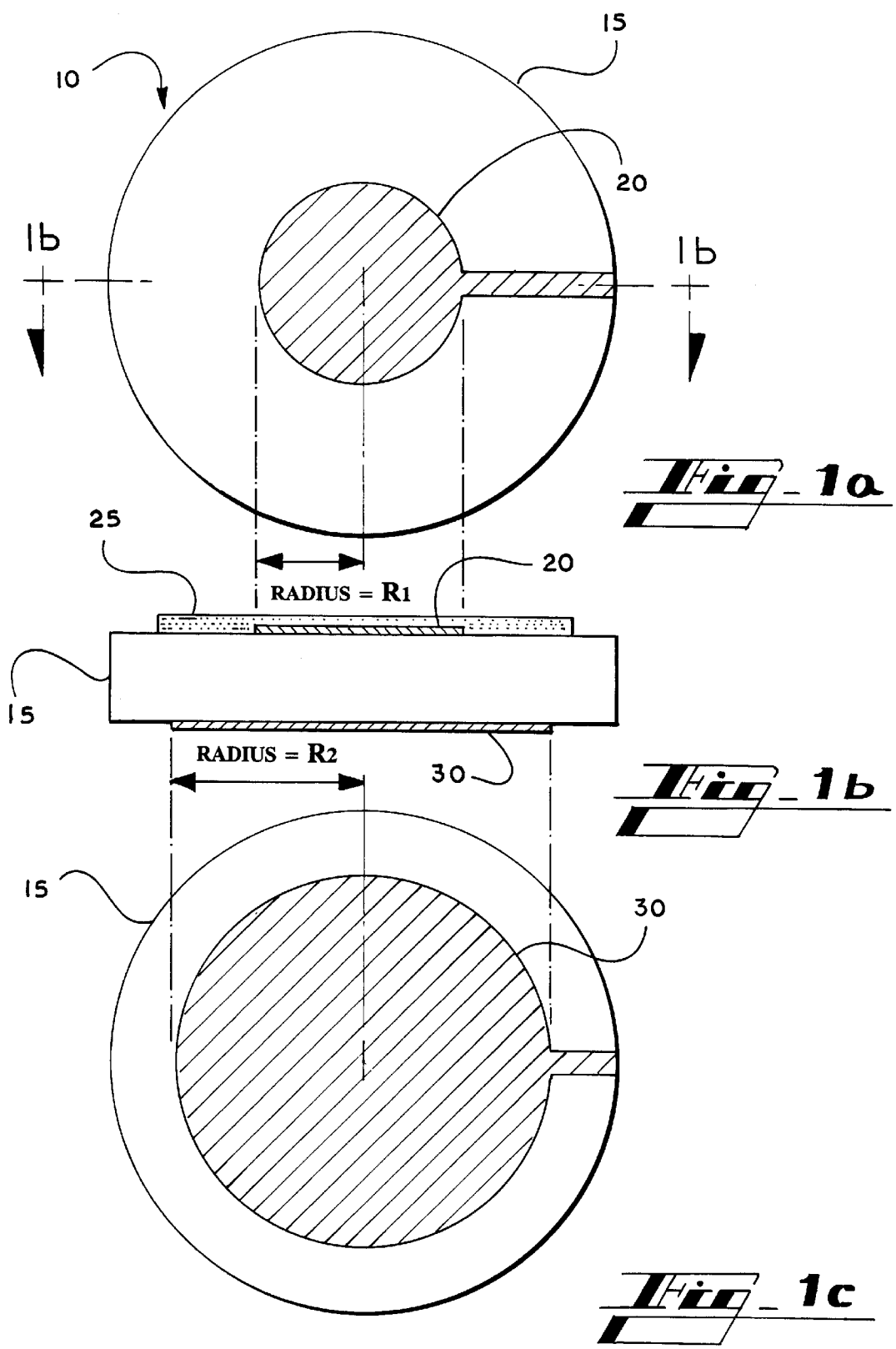

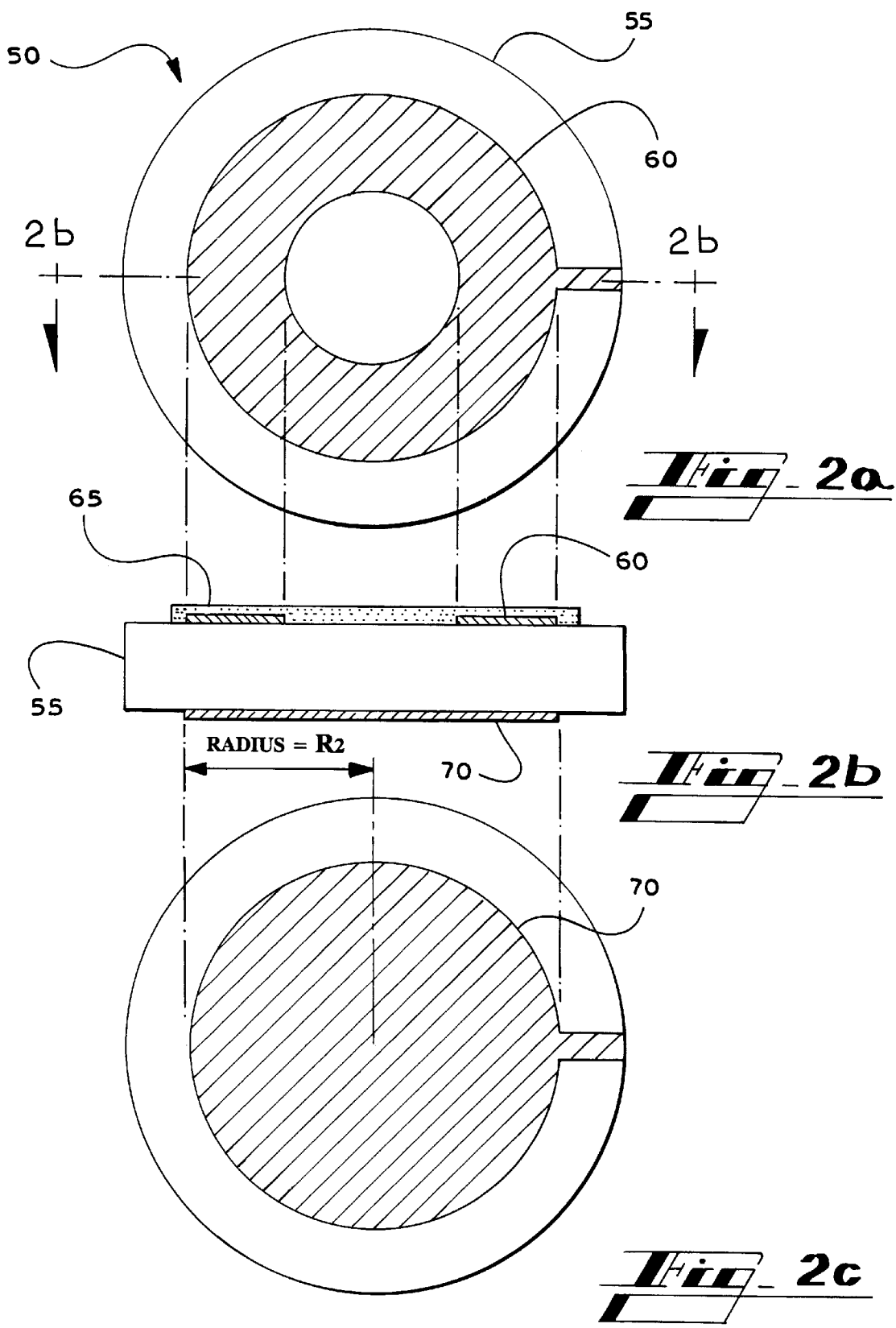

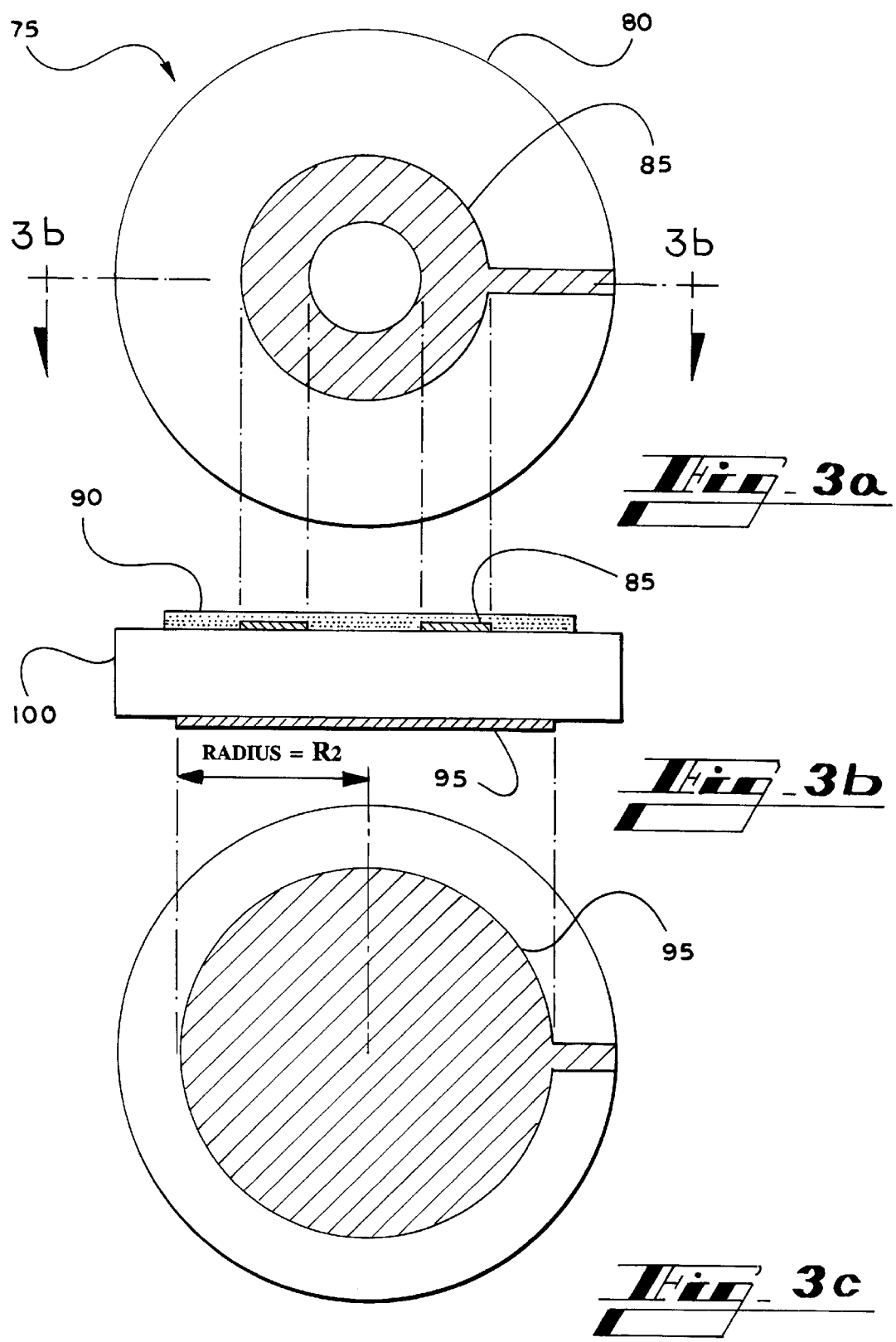

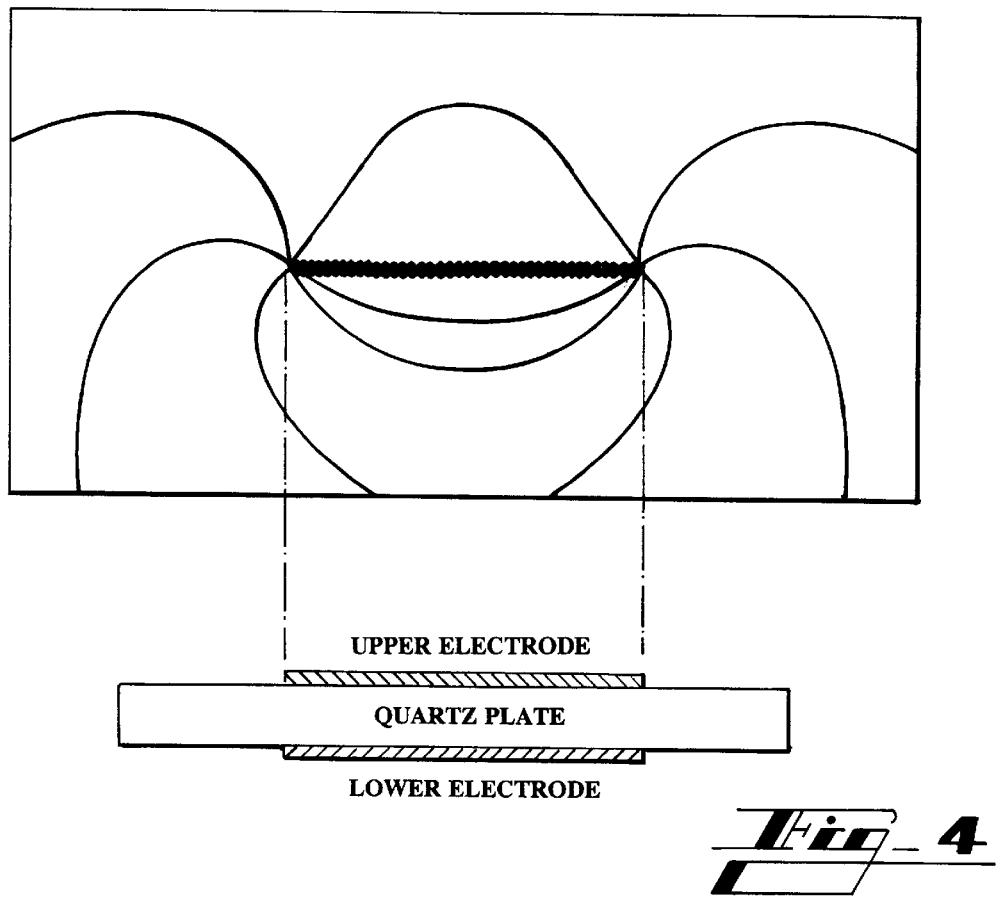
FIG_4
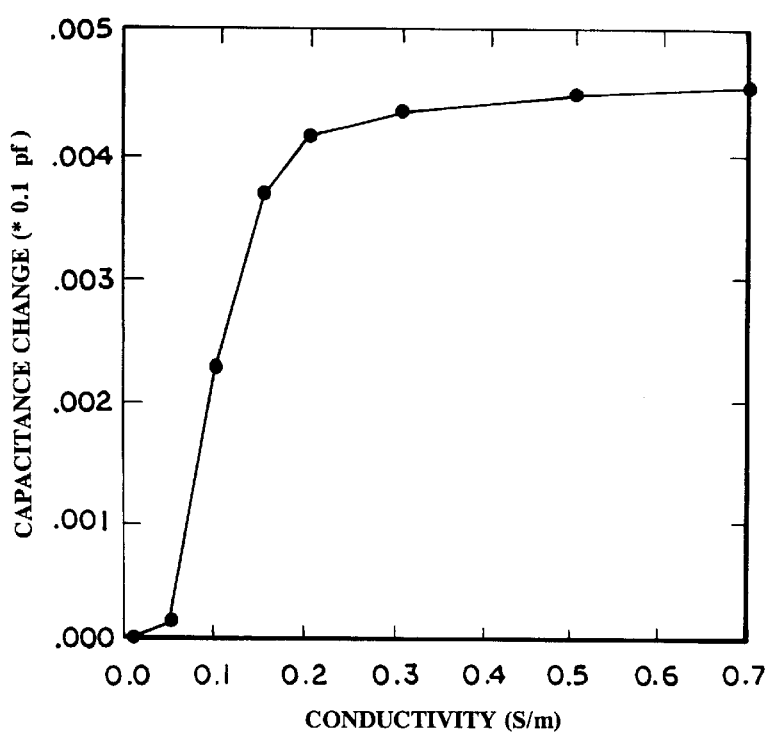
FIG_5

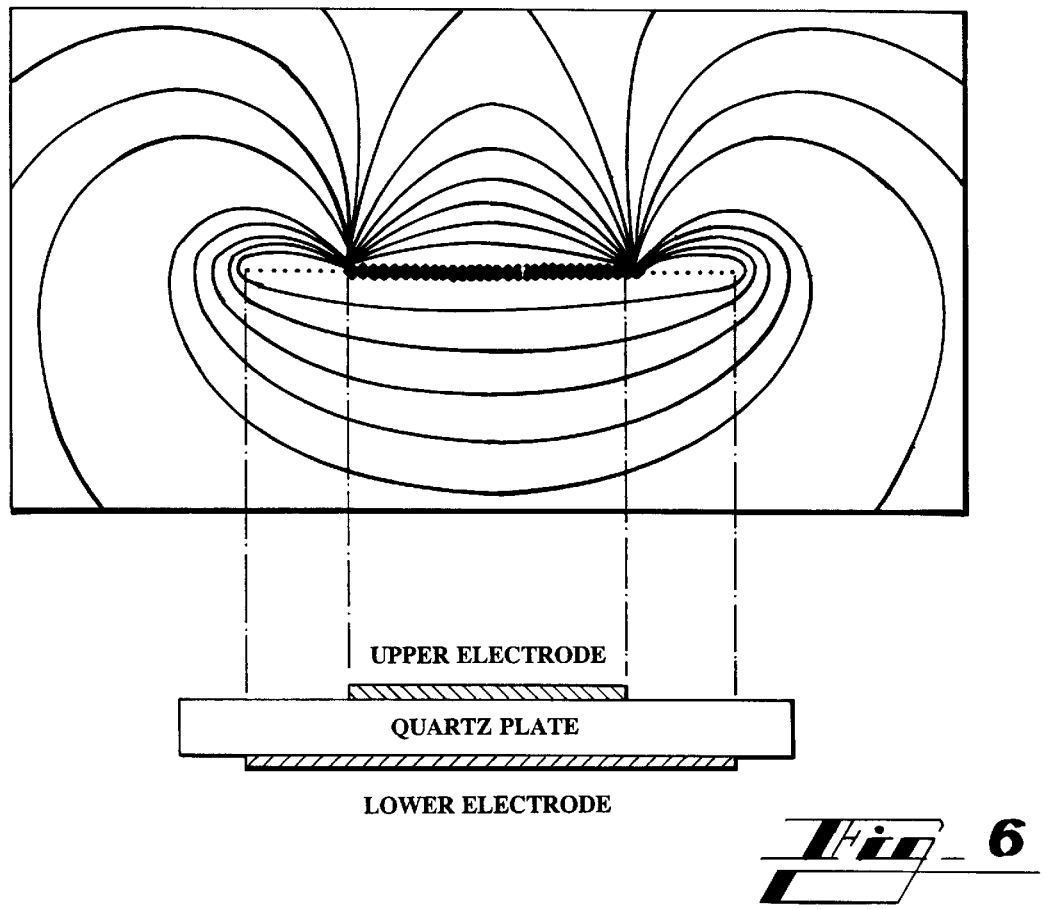
Fig_6
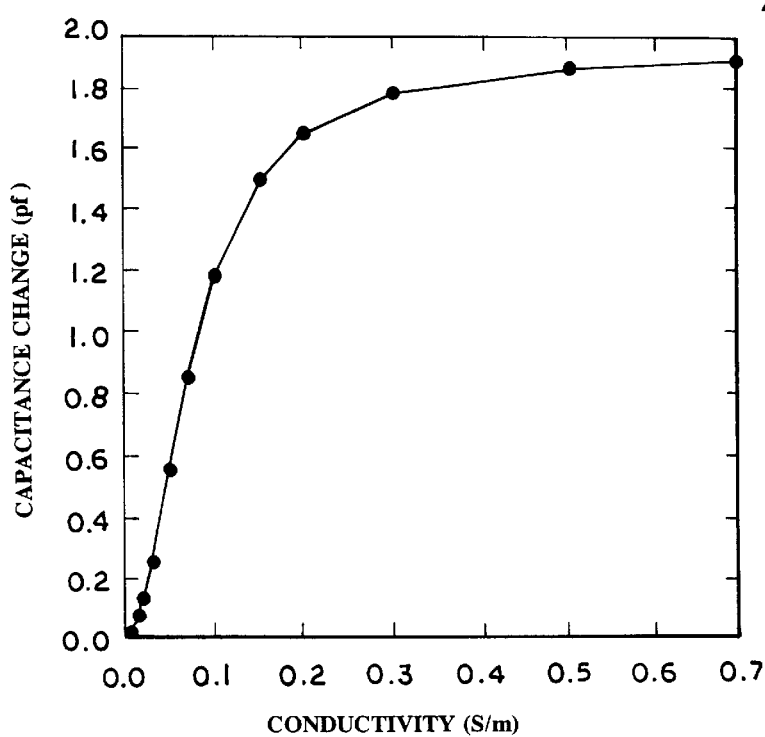
Fig_7

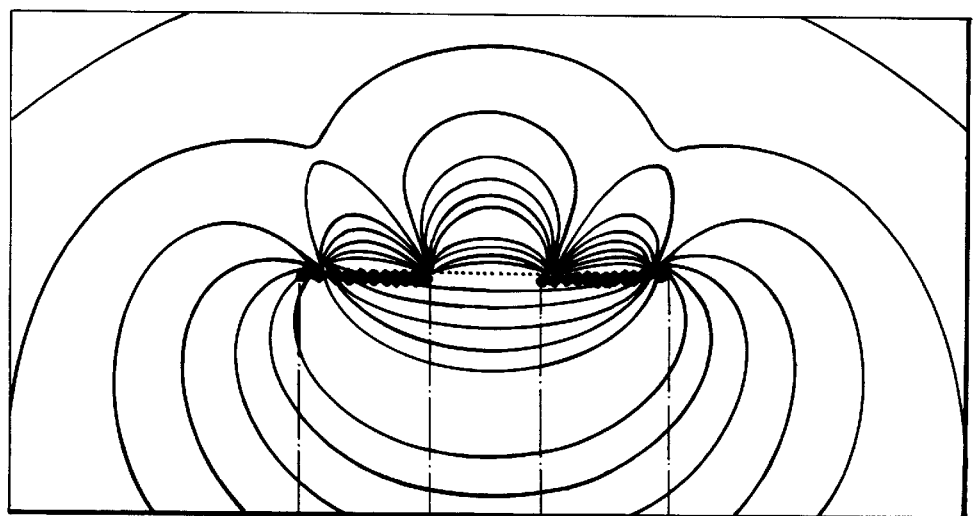
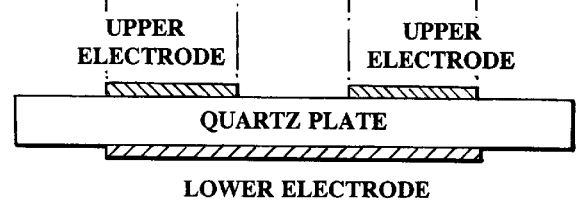
Fig. 8
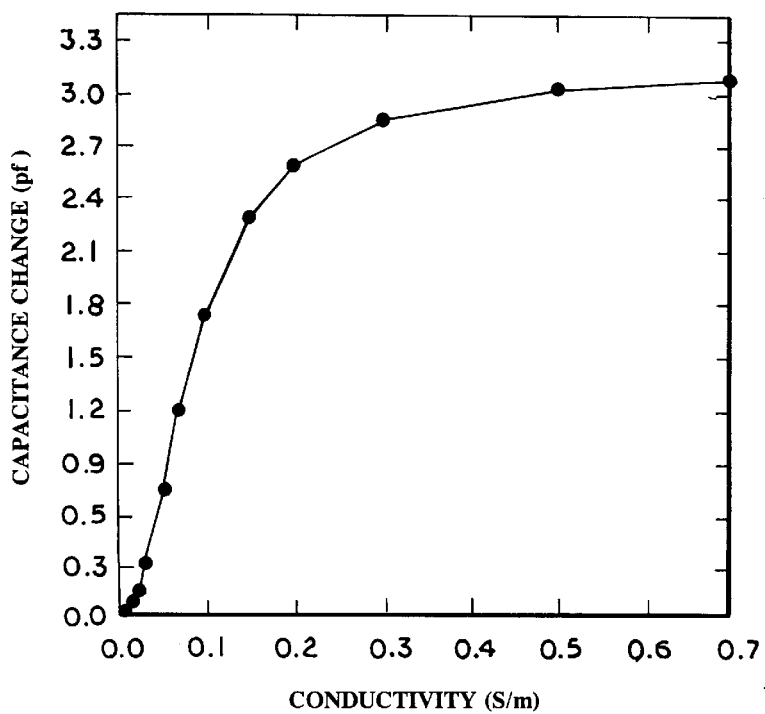
Fig. 9

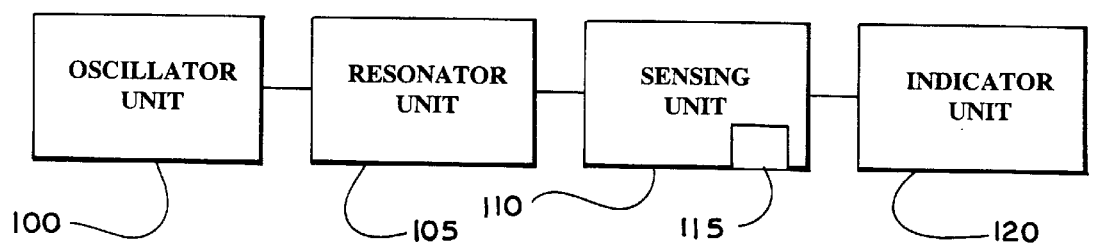
Fig_10
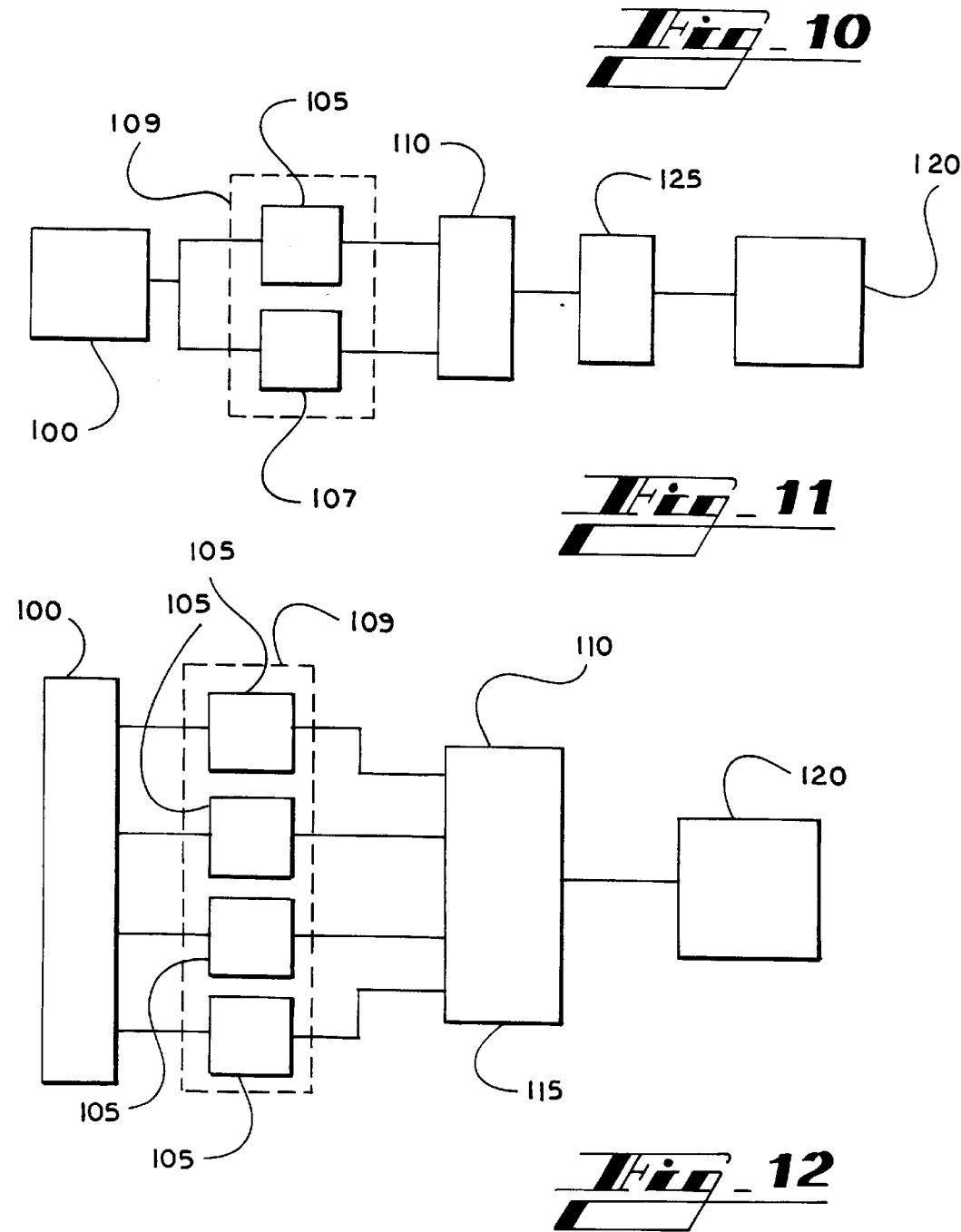
Fig_11
Fig_12

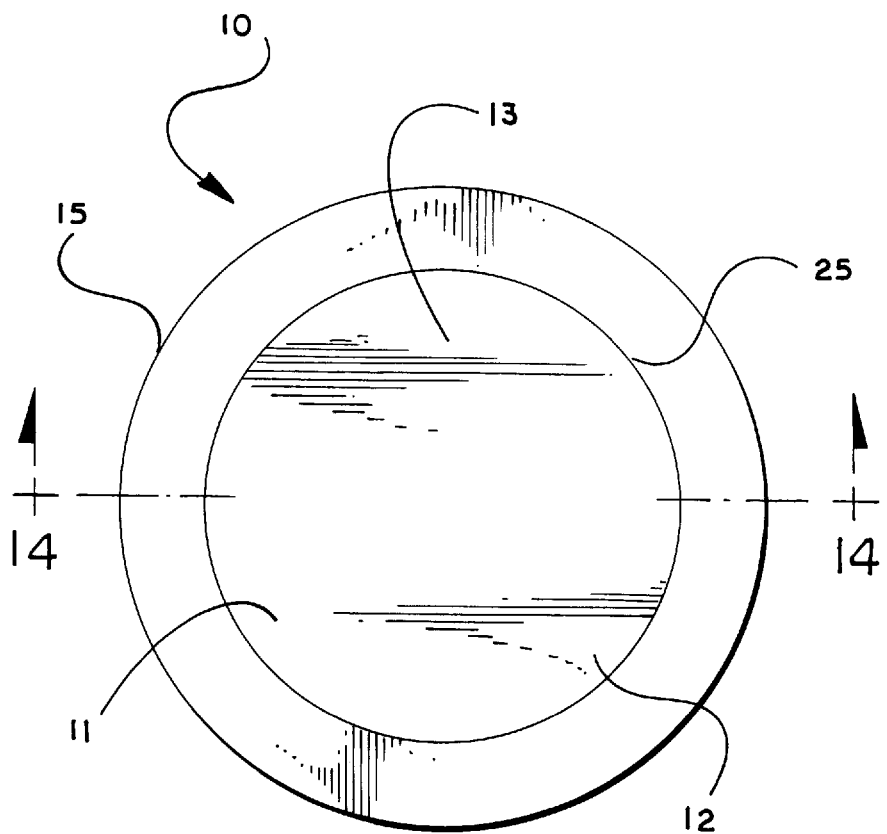
Fig_13
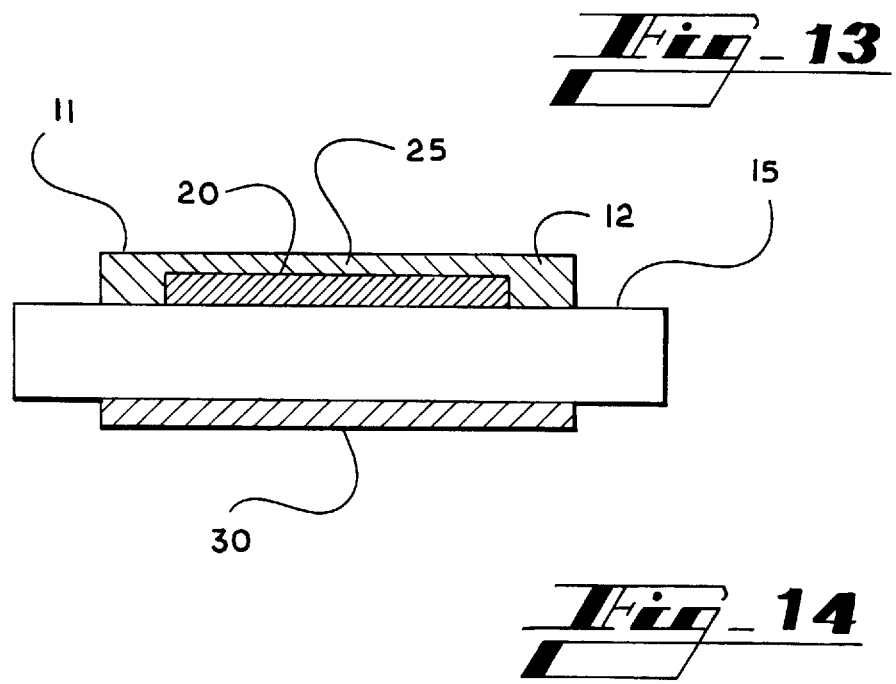
Fig_14

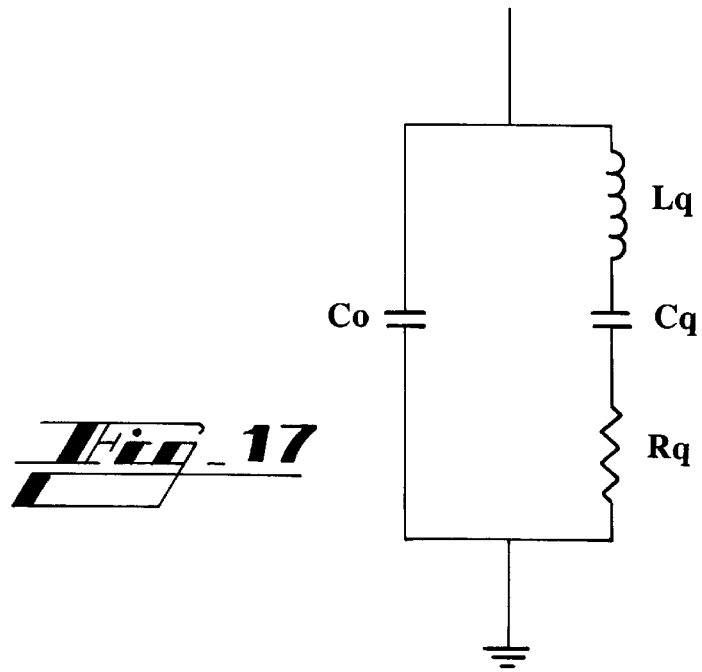
Fig_17
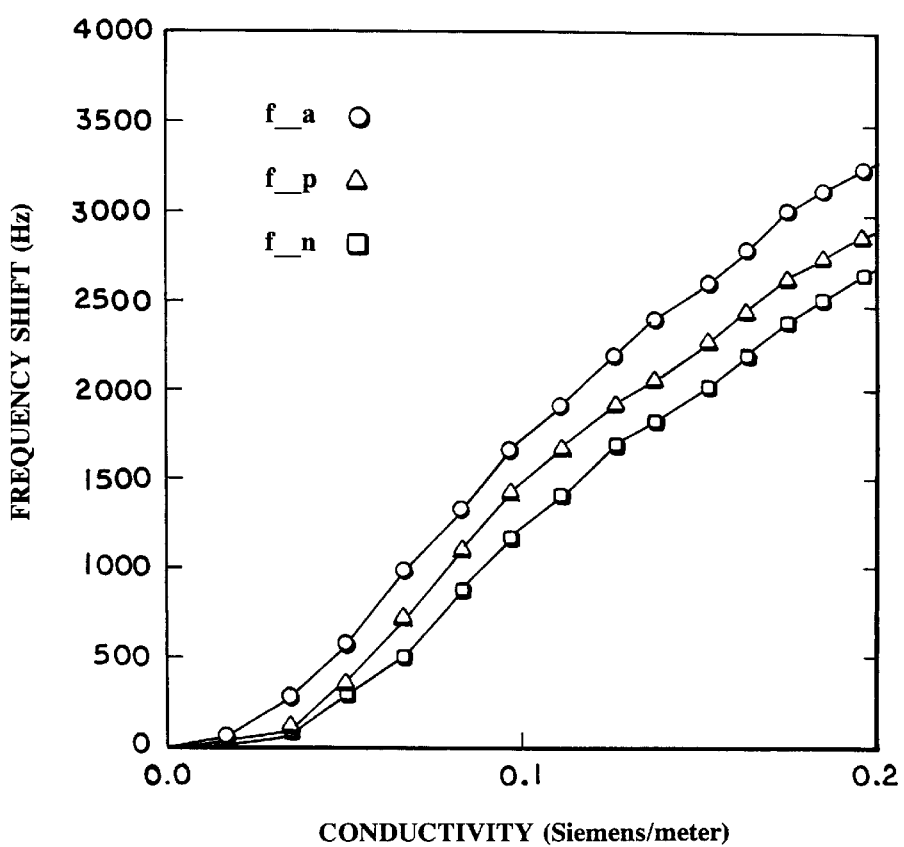
Fig_19

PIEZOELECTRIC RESONATOR CHEMICAL SENSING DEVICE

FIELD OF THE INVENTION

This invention relates generally to methods and apparatus for measuring small concentrations of an analyte in a medium. More particularly, the present invention measures changes in electrical properties of a coated piezoelectric resonator in the presence of an analyte. The sensor of the present invention optionally has a polymeric layer which experiences changes in electrical properties and/or mass when the device is contacted by a particular analyte in a medium. Changes in the resonant and/or anti-resonant frequencies of the piezoelectric resonator indicate the presence of, and can indicate the quantity of, the analyte in the medium.

BACKGROUND OF THE INVENTION

Various gases and particles, which often go unnoticed even at a dangerous level, are increasingly being found in biological and chemical manufacturing settings and in human living and working environments. These gases include volatile organic compounds (VOC) and chlorinated hydrocarbons (CHCs) in air. Chlorinated hydrocarbons are low molecular weight organics compounds released in the air by most cleaning solvents.

Examples of particles which can be found in air are dust mite antigen contaminated particles. Dust mite antigen contaminated particles are biogenic particles, found in house dust, contaminated with dust mite feces. Dust mites are arachnids and are commonly found associated with humans. CHCs and dust mite antigen contaminated particles are two examples of target analytes which must be filtered out of the environment since they seriously compromise indoor air quality. Airborne transmission of these particles, which occurs during house cleaning (vacuum sweeping), is known to result in strong allergic reactions in most humans. Filtration of these pollutants from the living or working environment, however, can only be effective if it is complemented by a monitoring of these compounds.

Interactive "smart" filters incorporate detection and monitoring with filtration. Such "smart" filters, reinforce consumer confidence and simulate consumer interest and will play an important role in the near future of indoor air pollution control. Chemical sensors which can be exposed to a natural, unfiltered sample gas/particles are needed. Such sensors will require good selectivity or molecular recognition for the chemical species or particles whose detection, quantification and then filtration are desired. These sensors should be able to communicate to the observer (or a system which could activate the filtration process) data associated with processes which may be in the molecular level to the parts per million or billion range.

Various types of microsensors utilizing electrical, optical, acoustical and electrochemical technologies have been successfully employed in a variety of applications. Perhaps the most sensitive of all the microsensors are acoustic sensors, particularly those using surface acoustic wave (SAW), bulk acoustic wave (BAW), and acoustic plate modes (APM). In recent years, acoustic wave devices have been investigated as the sensing element in gas and liquid-phase detector applications. Acoustic wave detector applications include selected chemical sensors and biosensors. In these selective microsensors, selectively is typically achieved by coating a thin polymeric or metallic film on the sensing surface of the piezoelectric crystal. The polymer may be organic, inorganic or organometallic.

Acoustic wave chemical sensors and biosensors thus consist of a piezoelectric crystal device and a chemical system attached to the crystal surface. The chemical system consists of the polymeric coating and/or chemoreceptors attached to the coating. The chemical system is used as a molecular recognition element and has the ability to selectively bind molecules and gas particles. While the physics of the detection process is very complex, the principle of operation of acoustic wave device sensor is quite simple and the results are reliable. An acoustic wave confined to the surface (SAW) or bulk (BAW) of a piezoelectric substrate material is generated and allowed to propagate. Any matter that happens to be present on the crystal surface will perturb that surface in such a way as to alter the properties of the wave (i.e. velocity or frequency, amplitude or attenuation). The measurement of changes in the wave characteristics is a sensitive indicator of the properties of the material present on the surface of the device. In general, it is well known that both mechanical and electrical perturbations of the surface affect the propagating acoustic waves and result in sensing. Such perturbations result from the absorption or diffusion of gas into the film; molecule selectivity, migration or binding; and formation of complexes within the film.

Prior art devices have focused on the mass loading effect in the implementation of those devices. In those devices, the gas is absorbed by the film thereby increasing the mass of the film and change the wave frequency and/or attenuation. The change in frequency has been shown to be a direct function of the amount of gas absorbed. Because the added mass is very small, the acoustic wave perturbation may be small.

Piezoelectric materials are materials which generate electricity when subjected to mechanical stress and, conversely, generate mechanical stress when a voltage is applied. There are many materials which are piezoelectric. These piezoelectric materials have found application in many diverse technologies, ranging from mechanical actuators and gas, igniters to very precise timekeeping device.

The uses for piezoelectric devices derive from the conversion of electricity to motion or vibration and, often the reconversion of that motion back into electricity. For example, a precision clock oscillator will utilize a quartz crystal of very precise dimension and mass. Electrodes are formed on the surface of the crystal, an electric field is applied. This stimulates a mechanical stress in the quartz.

If the applied voltage changes at or near the resonant frequency of the crystal, a sustained vibration may be generated in the quartz. At the resonant frequency of the quartz which may be determined by cut angle, thickness, Length, width and mass, impedance is minimized with little electrical loss. Outside of this frequency, larger losses will occur and impedance is changed.

The Q of a crystal is a measure of how narrow a band of frequencies is passed by the crystal with minimum attenuation relative to the resonant frequency of the crystal. Often the Q of a piezoelectric material will determine the useful application. For example, very low Q materials are capable of converting wide frequency bands to and from mechanical energy. These materials are often used in sonic transducers in applications such as in microphones or speakers. The low Q allows for many tones to be produced.

Other applications demand a great deal of precision, such as timekeeping. For these applications, a material with a very high Q is preferred, since only a very narrow band of frequencies may then be passed through the piezoelectric material. In these precision applications, the piezoelectric material is usually associated with an electronic oscillator circuit, where the oscillator circuit will be caused to oscillate at the resonant frequency of the piezoelectric material.

With modern manufacturing methods, precision crystals of quartz or similar very high Q materials may be made to oscillate at a frequency which is accurate to within a few parts per million. As noted above, this frequency is dependent upon the type of material, mass and dimensions of the crystal resonator During the production of the quartz resonators, layers of conductive electrode material are typically deposited to a precision of only a few atomic layers, since the resonators will be sensitive to changes in mass as small as this.

The characteristic sensitivity of high Q piezoelectric materials to changes in mass has led industry to a number of diverse applications. For example, a quartz resonator may be coated with an absorbent which is selective to a particular compound. The amount or concentration of that compound may be determined just by monitoring the change in resonant frequency of the quartz as the compound is absorbed. As more of the compound is absorbed, the mass of the vibrating structure is increased Piezoelectric quartz crystal resonators, in which thickness-shear horizontal vibrations (BAW) are excited to set up standing waves, having been used as detectors in both gas and liquid environments. In gas-phase applications, one or both surfaces of the crystal can be exposed to a medium containing an analyte. For example, in a sodium chloride solution, sodium can be the analyte to be measured. The quartz crystal resonator functions as a mass sensitive detector. The frequency change of the resonator describes loading due to the added mass of the analyte. By exposing the vibrating crystal surface to liquids, mechanical properties of the liquids, such as mass, density, and viscosity can be quantified.

Piezoelectric quartz crystal resonators (QCR), in which thickness-shear horizontal vibrations are excited to set-up standing waves, have been investigated and used as detectors in both gas and liquid environments. In gas- and liquid-phase applications two identical electrodes are used, with one or both surfaces of the crystal coated with a layer and exposed to the analyte to be measured. In those applications, the QCR is used as a mass detector. In these prior art devices, only the series resonant frequency, $f_s$, is measured and related to the added mass, hence to the concentration of analyte being measured. To date, all QCR based chemical sensors are used as mass detectors in which the added mass caused by the adsorbed molecules is measured. However, because the added mass is usually very small, sensitivity is low, typically $\mu g/cm^2$ of electrode surface. Moreover, because only the series resonant frequency, $f_s$, is measured and since most coatings react to a class of molecules rather than one molecule, selectivity is limited. When the coated device is exposed to the target molecules of a gas or a liquid, a reaction taking the form of binding and/or diffusion of these molecules occurs.

What is needed is a sensor that is more sensitive, more selective and can provide analyte specific chemical information than the prior art sensors. The sensor should be able to measure not only changes in mass but also changes in electrical properties caused by either binding or conversion of an analyte on the surface of the sensor thus providing a multi-information chemical sensor. Indeed, changes in electrical properties of coatings could add to the selectivity process.

SUMMARY OF THE INVENTION

The present invention comprises a sensor for measuring an analyte in a medium comprising a piezoelectric resonator having a first side with an electroded region and a second opposing side having an electroded region that is different in size and/or shape of the first electrode. The present invention is capable of measuring more than one parameter thereby providing a multi-information sensing device. In other words, the second electroded region has a different geometry than the first electrode.

The first side of the sensor of the present invention has desirably an essentially round electrode that covers a substantial portion of the piezoelectric resonator. On the second opposing side, the electrode can be virtually any geometry and can be a combination of shapes as long as the second electrode is different in size or shape from the first electrode. The term "geometry" as used herein means the surface area and shape (configuration) of the electrodes on the piezoelectric surface. The surface area and shape are such that the electric fringing fields are enhanced while still maintaining vibration stability under loading by the polymeric material. For example, the second electrode can be an essentially round disk that is smaller than the electrode on the first side. In another embodiment, the second electrode can be a ring that has the same diameter or a different diameter as the disk on the first side of the piezoelectric resonator. It is to be understood that the second electrode may have any shape or any size that is different from the first electrode. The electrode is desirably gold but can be other conductive substances such as silver and aluminum.

A polymeric layer may optionally be deposited on the second side or the sensing side of the resonator, at least a portion of the polymeric layer being deposited in the electroded region. The composition of polymeric layer is any composition that selectively binds to or reacts with an analyte of interest in the medium. The polymeric layer may change in viscoelasticity, or may change in mass, either increasing or decreasing in mass in response to the analyte in the medium or may change in conductivity or in dielectric constant. The polymeric composition may contain a molecule which selectively binds to a particular analyte in a medium. These molecules include, but are not limited to, antibodies, fragments of antibodies, receptors for various molecules, and the like.

Analytes to be measured include, but are not limited to, compounds such as trichloromethane, tetrachloromethane, trichloroethane, trichloroethylene, tetrachloroethane, tetrachloroethylene, and toluene. Analytes also include, but are not limited to, proteins, small organic molecules, substrates for enzymes, and the like.

In operation, a sensing circuit compares at least one resonant frequency and at least one anti-resonant frequency with stored reference frequencies. Differences between the sensed frequencies and the stored reference frequencies indicate the presence and/or concentration of the analyte in the medium. The electrical sensing circuit sweeps frequencies in a band containing the respective resonant and anti-resonant frequencies and can sense changes in the resonant and anti-resonant frequencies in response to the presence of the analyte in the medium. The sensed resonant and anti-resonant frequencies indicate mass density, viscosity, and dielectric constant and conductivity changes in the polymeric layer as a result of association of the analyte with the polymeric layer. It is to be understood that the measurement of the anti-resonant frequencies due to changes in the conductivity and dielectric constant of the polymeric layer is a critical feature of the present invention. As will be explained later, due to the lossy conditions, the anti-resonant frequencies consist of three frequencies, each with a different rate of variation with changes in the conductivity and dielectric constant of the polymer layer. This is an added parameter over the prior art for the identification and quantification of the analytes in the medium. This is made possible by the geometric configurations of the electrodes as described herein.

In other embodiments of the present invention, several piezoelectric resonators can be used in the same apparatus. The additional piezoelectric resonator sensors can be designed to measure additional analytes in the medium and thereby the device can simultaneously measure two or more analytes in the medium depending on how many piezoelectric resonators are present in the device.

In yet another embodiment, the polymeric layer has a first zone comprising a first polymer composition, and opposing second zone comprising a second polymer composition, and a third central gradient zone between the first and second zones comprising a graduated combination of the first and second polymer zones. The first, second, and central zones are juxtaposed in generally side-by-side relationship on the first side of the piezoelectric resonator. The sensitivity of each respective zone in the polymeric layer can optionally respond differently to different analytes. In other words, the first and second polymer compositions in the polymeric layer can include different polymers that are selective to different analytes.

It is to be understood that the piezoelectric resonator sensor does not have to have a polymeric layer. The series resonant frequency changes when the medium contacting the first electrode has sufficient conductivity to form an effective electrode in combination with the first electrode. The effect on the electrical properties in the medium is similar to having the first electrode cover substantially the entire first side of the piezoelectric resonator, i.e., identical electrode geometries. Changes in antiresonant frequency are primarily caused by changes in conductivity and dielectric constant in the medium and not primarily caused by mass loading of the piezoelectric resonator.

In yet another embodiment of the present invention, the piezoelectric resonator sensor can detect the condition of a filter in a processing stream by sensing properties of the analyte in a medium passing through the filter. The present invention includes a first piezoelectric resonator sensor upstream from the filter and a second piezoelectric resonator filter downstream from the filter. A sensing circuit senses at least one resonant frequency and at least one anti-resonant frequency for each of the first and second resonators and compares the respective resonant and anti-resonant frequencies thereby providing an indication of the filter condition. A filter failure indication occurs when the compared frequencies of the two piezoelectric resonator sensors are substantially the same.

These and other objects, features and advantages of the present invention will become apparent after a review of the following detailed description of the disclosed embodiments.

BRIEF DESCRIPTION OF THE DRAWINGS

FIG. 1 shows a first embodiment of the piezoelectric resonator sensor of the present invention.

FIG. 1a is a top view of the second opposing side with the electroded region shown in black.

FIG. 1b is a cutaway view of the piezoelectric resonator sensor along line 1b—1b with the electroded region represented as black.

FIG. 1c is a bottom view of the piezoelectric resonator sensor with the electroded region shown as black.

FIG. 2 is a second embodiment of a piezoelectric resonator sensor of the present invention.

FIG. 2a is a top view of the second opposing side with the electroded region shown in black.

FIG. 2b is a cutaway view of the piezoelectric resonator sensor along line 2b—2b with the electroded region represented as black.

FIG. 2c is a bottom view of the piezoelectric resonator sensor with the electroded region shown as black.

FIG. 3 is a third embodiment of a piezoelectric resonator sensor of the present invention.

FIG. 3a is a top view of the second opposing side with the electroded region shown in black.

FIG. 3b is a cutaway view of the piezoelectric resonator sensor along line 3b—3b with the electroded region represented as black.

FIG. 3c is a bottom view of the piezoelectric resonator sensor with the electroded region shown as black.

FIG. 4 is a diagram of equipotential field lines for a QCR device with equal circular electrodes.

FIG. 5 is a graph of the electrostatic capacitance changes vs. conductivity for a QCR device with identical circular electrodes.

FIG. 6 is a diagram of equipotential field lines for the QCR device shown in FIG. 1.

FIG. 7 is a graph of the electrostatic capacitance changes vs. conductivity for QCR device shown in FIG. 1.

FIG. 8 is a diagram of equipotential field lines for the QCR device shown in FIG. 2.

FIG. 9 is a graph of the electrostatic capacitance changes vs. conductivity for QCR device shown in FIG. 2.

FIG. 10 is a block diagram of a sensing apparatus including a piezoelectric resonator unit of the invention.

FIG. 11 shows a block diagram of a second embodiment of the sensing apparatus including a reference piezoelectric resonator unit.

FIG. 12 shows a block diagram of a third embodiment of the sensing apparatus including a plurality of piezoelectric resonator units.

FIG. 13 shows a third embodiment of the piezoelectric resonator unit having a gradient polymeric sensing layer.

FIG. 14 shows a cross-sectional view taken at 15—15 of FIG. 13.

FIG. 17 shows the equivalent circuit of a typical uncoated QCR with two identical electrodes.

FIG. 19 shows the changes in the parallel resonance frequency vs. conductivity.

DETAILED DESCRIPTION OF THE INVENTION

Figure 15:
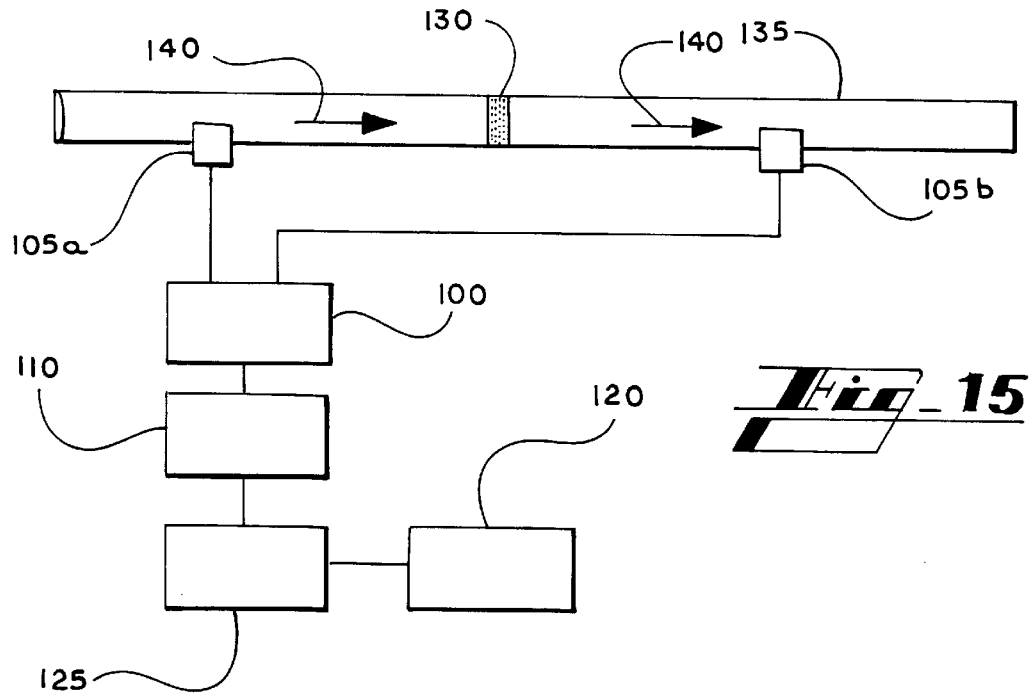
FIG. 15 shows a filter failure sensing apparatus including piezoelectric resonator units on opposites sides of a filter.

The present invention relates to selective sensor for detecting and determining the concentration of an analyte in a medium. The analytes may be, for example, gas molecules that may be part of selected pollutants which need to be monitored in human working and living environments. The sensor is also suitable for use as a chemical specific detector in liquid environments.

The sensor of the present invention is desirably a quartz crystal resonator (QCR) with modified-electrodes on the sensing surface that are dissimilar in shape or geometry to the electrode on the opposing side of the resonator and includes a chemically sensitive functionalized polymer layer selected to react with the molecules or class of molecules to be measured. When a signal is applied to the device, a vibration of the crystal occurs together with a relatively strong electric field in the non-electroded area, which interacts with the chemically reactive polymer.

The present invention includes exposing the coated surface of the device to the molecules to be measured causing the electrical properties of the layer to change. Such changes are caused by the binding or diffusion of the molecules(s) in the layer, and result in a change in the dielectric constant and conductivity as well as in the well known mass and viscoelastic constant of the layer. The change in these parameters result in a variation of all critical frequencies of the QCR which can be simultaneously monitored and related to the concentration of the target molecules.

The sensor device of the present invention desirably employs a QCR with modified-electrode on one of its surfaces. The two electrodes are desirably made of a gold layer on a thin chromium layer. The two electrodes are dissimilar both in geometrical shape and/or dimension. Examples of such electrodes are shown in FIGS. 1 through 3 for three types of such QCRs. In these examples, the QCR employs two concentric circular electrodes with the electrode on the sensing surface having a smaller radius $r_1 < r_2$ ($r_2$ is the radius of second electrode) (FIG. 1) or a ring shape configuration (FIGS. 2 and 3). A chemically sensitive functionalized polymer layer is optionally deposited on the modified-electroded surface covering both electroded and nonelectroded areas. Certain aspects of the piezoelectric resonant sensors with dissimilar electrodes are disclosed in U.S. Pat. No. 5,455,475 to Josse, et al. and this patent is incorporated by reference in its entirety.

Referring now to FIG. 1, the piezoelectric resonator 10 has a circular upper electrode 20 (FIG. 1a) and a circular opposing lower electrode 30 on a quartz base 15 (FIG. 1b). The upper electrode 20 is concentric and is smaller in diameter than the lower electrode 30. The piezoelectric resonator 10 also has a polymeric layer 25 that is layered over sensing electrode 20 (FIG. 1b). The polymeric layer 25 typically is larger than the sensing electrode 20. Referring to FIG. 2, the piezoelectric resonator 50 has a ring upper electrode 60 and a circular opposing lower electrode 70 on a quartz base 55. The piezoelectric resonator 50 also has a polymeric layer 65 that is layered over sensing ring electrode 60. (FIG. 2b) The polymeric layer 65 typically is larger than the sensing ring electrode 60. Referring to FIG. 3, the piezoelectric resonator 75 has a ring upper electrode 85 and a circular opposing lower electrode 95 on a quartz base 80. In this embodiment of the present invention, the ring upper electrode 85 is smaller in diameter than the electrode 95. The piezoelectric resonator 75 also has a polymeric layer 90 that is layered over sensing ring electrode 85. (FIG. 3b) The polymeric layer 90 typically is larger than the sensing ring electrode 85. Typically, the upper electrode in the disclosed embodiments is the sensing electrode and is the electrode that is exposed to the medium with the analyte to be measured. However, it is to be understood that both electrodes may be exposed to the medium in certain embodiments of the present invention.

The present invention comprises a piezoelectric resonator sensor that is capable of measuring an analyte or a multiplicity of analytes in a medium. As used herein, the term "analyte" means an atom, ion, molecule, macromolecule, organelle, or cell that is detected and measured. The term "analyte" also means a substance in a medium including, but not limited to, environmental contaminants such as trichloromethane, tetrachloromethane, trichloroethane, trichloroethylene, tetrachloroethane, tetrachrloroethylene, toluene, benzene, aromatic compounds and hydrocarbon pesticides. Analytes include molecules, such as proteins, glycoproteins, metal salts, ions, and the like. The term "analyte" also includes neurotransmitters, hormones, growth factors, cytokines, monokines, lymphokines, nutrients, enzymes, and receptors. The term "analyte" also means structured elements such as macromolecular structures, organelles and cells, including, but not limited to cells of ectodermal, mesodermal, and endodermal origin such as stem cells, blood cells, neural cells immune cells, and gastrointestinal cells, and also microorganisms, such as fungi, viruses, bacteria and protozoa.

The term "medium" as used herein means an aqueous medium, a non-aqueous liquid medium, and gases.

Polymeric sensing layers can comprise a variety of monomer units including siloxanes, alkane thiols, urethanes, and epichlorhydrans. Examples of sensing layer materials are set forth in "Patterning Self-Assembled Monolayers Using Microcontact Printing: A New Technology for Biosensors?," by Milan Mrksich and George M. Whitesides, published in TIBTECH, June, 1995 (Vol. 13), pp. 228–235, hereby incorporated by reference.

The term "polymeric layer" as used herein means a layer comprising a material including, but not limited to poly (diphenylmethylsiloxanes), poly(etherurethanes), poly (epichlorohydrans), and poly(1, 1, 1-trifluoropropylmethyl siloxanes) and polyolefins. These same materials can be modified by incorporating molecular groups which will enhance selectivity toward target analytes. Moreover, metallo-organic materials, such as metallo-phthalocyanine, whose conductivity can undergo changes when in contact with an analyte, represent other materials which can be used. The composition of the polymeric layer is selected from compositions functionally operable to provide a change in a resonant or anti-resonant frequency of the piezoelectric resonator in response to at least one of presence and concentration of the analyte at the polymer layer. The term "polymeric layer" also means a layer with a selective moiety for a particular analyte incorporated therein or thereon. The selective moiety includes, but it not limited to, antibodies, fragments of antibodies that are capable of binding an analyte, biological receptors for particular analytes, biotin, avidin, strep A protein, and enzymes. The polymeric layer can cover part of the electrode, all of the electrode or can extend beyond the boundaries of the electrode on the piezoelectric resonator.

The total field contributing to the interaction consists of two components: (1) the surface fringing field due to the asymmetric configuration of the electrodes and potential difference between the two electrodes, and (2) the electric field associated with the acoustic wave in the free surface region opposite the lower electrode. However, because quartz is a weak piezoelectric material, the latter can be assumed negligible and the interaction is primarily due to the fringing fields.

The present invention makes use of electric fields and electric potentials found everywhere around the quartz crystal resonators that are used in the sensors of the present invention. These fields have been graphically visualized by using the finite element and analysis method. (J. R. Brauer, "What Every Engineer Should Know about Finite Element Analysis" Marcel Dekker, Inc., New York, 1990) The graphical visualization of the fields shows the electrical sensing mechanism of the piezoelectric resonator sensor of the present invention. (See FIGS. 4, 6, and 8)

The surface electric fields and surface electric potentials along the interface between the piezoelectric resonator sensor of the present invention and the polymeric layer can also be analyzed in this way. The changes in the electrostatic capacitance due to the changes in the electrical material properties of the polymeric layer, or loading medium, can also be calculated. FIG. 4 shows equipotential field lines associated with a prior art piezoelectric resonator sensor wherein the electrodes on either side of the quartz crystal are the same size. As shown in FIG. 4, although the conductivity of the loading medium increases, the changes in the surface fringing fields are insignificant. As a result, the changes in the capacitance also become insignificant. (See FIG. 5) In FIG. 6 is a diagram of equipotential field lines for the QCR device shown in FIG. 1. As shown in FIG. 1, there exists strong infringing fields along the surface of the partially electroded region. These surface fringing fields are perturbed by changing the electrical properties of the loading medium. The strong fringing fields near the edge of the upper electrode in FIG. 6 are due to the high concentration of the electric charges at the edge of the upper electrode. However, when the loading medium is pure water, the electric fringing fields at the edge of the upper electrode are then suppressed by the high dielectric medium. The result is that the electric fields are extended along the surface of the partially electroded region.

As shown in FIGS. 6, 8 and 10, large portions of the electric potential fields are extended into the partially electroded region. However, there are still electric fringing fields near the upper electrode and the surface along the unelectroded region. When the conductivity of the dielectric loading medium is increased, the remaining electric fringing fields at the surface of the piezoelectric resonator sensor of the present invention are further suppressed. The modified-electrode piezoelectric resonator sensor of the present invention then becomes an almost perfect parallel plate capacitor with two identical electrodes when the conductivity is increased to 0.7 (S/m)

FIG. 5 is a graph of the electrostatic capacitance changes vs. conductivity for a QCR device with identical circular electrodes. As shown in FIG. 5, there are few equipotential field lines in this device when compared to the equipotential field lines generated by the devices included in the present invention and shown in FIGS. 6 and 8. As one increases the concentration of the loading medium, the change in conductivity induces changes in the capacitance. The results for the capacitance changes in various piezoelectric resonator sensors are compared in FIGS. 7 and 9. The graphs show that the modified-electrode piezoelectric resonator sensor of the present invention with larger partially electroded regions show greater changes in capacitance.

As shown in FIGS. 7 and 9, when the conductivity of the loading medium increases, the surface electric potential fields extend into the surface of the partially electroded region. When the conductivity of the loading medium reaches about 0.5 (S/m), the quartz capacitor with the modified-electrode configuration behaves as a perfect parallel plate capacitor with identical electrodes on both sides. Therefore, it can be concluded that the increase in the conductivity of the loading medium results in the expansion of the effective electrode surface area of the device. This, in turn, combined with the mass of the load should effect the particle displacement amplitude profile. The particle displacement amplitude profile becomes narrower with smaller upper electrodes and wider with larger upper electrodes. Therefore, the particle displacement amplitude profile becomes wider when the conductivity of the loading medium increases which in turn will modify the resonance condition of the piezoelectric resonator sensor of the present invention, hence also the antiresonent frequency.

Figure 16:
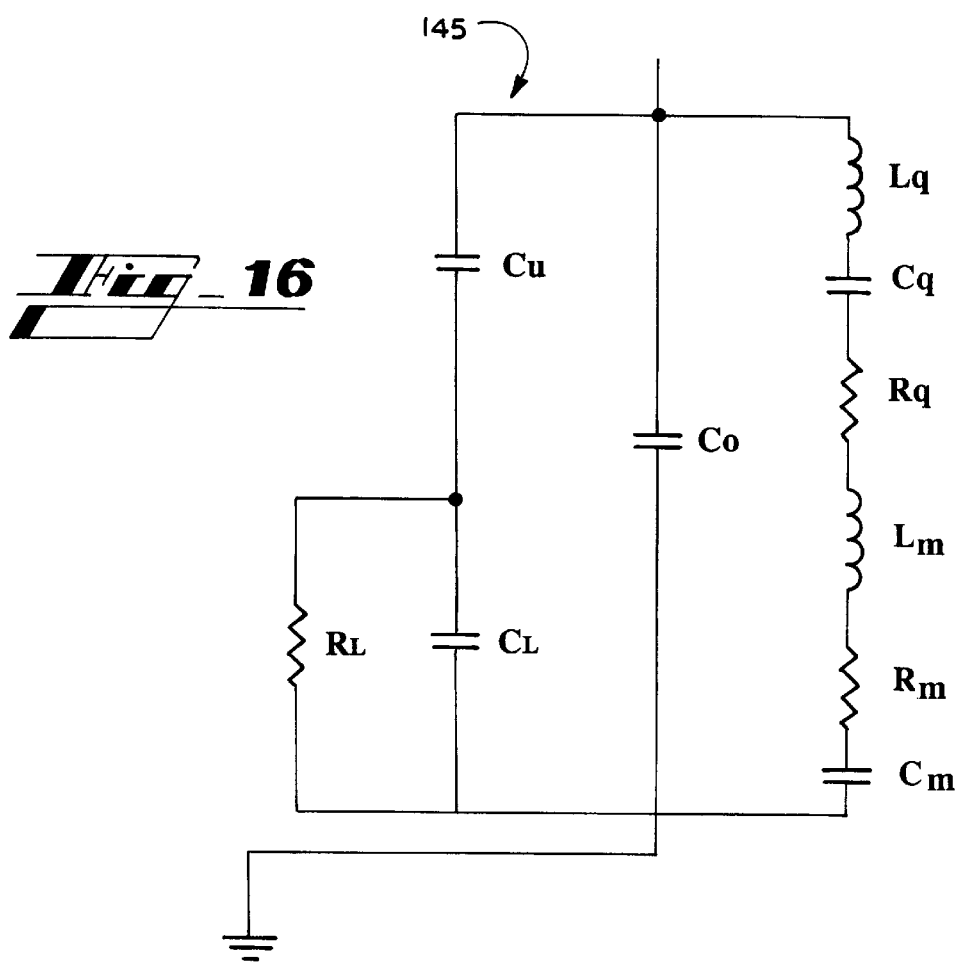
FIG. 16 shows a model electrical circuit for the piezoelectric resonator units of FIGS. 1–3.

FIG. 16 shows a diagram of a model equivalent circuit 145 for the piezoelectric resonators described in FIGS. 1 through 3. By analyzing this equivalent circuit, in the narrow range of frequencies at and near resonance and antiresonance, the critical frequencies can be defined. The admittance-impedance characteristics of the piezoelectric resonator units 105 (See FIG. 10 with specific embodiments shown in FIGS. 1 through 3) indicate changes in mechanical and electrical properties of the polymer layer 25 caused by a medium. Hence, one or more materials in the medium can be sensed.

For lossy piezoelectric resonators, as shown FIGS. 1 through 3, there are two mechanical mechanisms of energy dissipation. Mechanical energy is dissipated internally as modeled by internal motional resistance $R_q$, internal capacitance $C_q$, and internal inductance $L_q$, of piezoelectric resonator 10. Motional resistance $R_q$ represents the mechanical dissipation of piezoelectric resonator 10 (i.e. the conversion of electrical energy into heat through friction).

External mechanical energy dissipation results from the flow of electrical energy out of piezoelectric resonator unit 105 and into the adjacent medium in the form of acoustic waves. External mechanical properties are modeled as resistance $R_m$, inductance $L_m$, and capacitance $C_m$. These components correspond with mechanical loading of polymeric layer 25 mounted on piezoelectric resonator 10. This mechanical loading varies or changes with the viscosity, elastic constant and mass density of polymeric layer 25. Capacitance $C_m$ only affects the series resonant frequency $f_s$. Capacitance $C_m$ is incorporated into $C_q$ for purposes of the equations which follow later.

In FIG. 16, the external and internal mechanical vibrations which includes dissipation of energy are shown as a single branch having elements connected in series. This branch of model equivalent circuit 145 represents the mechanical properties or mechanical loading of piezoelectric resonator unit 105.

The other branches represent electrical properties of piezoelectric resonator unit 105. In a second branch, capacitance $C_o$ represents the electrostatic capacitance across piezoelectric resonator 10 between first and second electrodes 20, 30 in the fully electroded region and is a function of electrode size, shape and configuration, in other words, electrode surface area. In FIGS. 1 through 3, the fully electroded region represents the portions of electrode 20 that are within the projected outline of electrode 30.

In the third branch, capacitance $C_u$ represents the capacitance across piezoelectric resonator 10 (FIG. 1) in the partially electroded region. The value of capacitance $C_u$ varies as a function of the size, shape and configuration of the partially electroded region.

The electrical loading of polymeric layer 25 is represented by capacitance $C_L$ and resistance $R_L$ in parallel with each other. Capacitance $C_L$ is due to the dielectric constant of polymeric layer 25. Resistance $R_L$ represents the conductivity of polymeric layer 25.

In the third branch of the model equivalent circuit 145, the parallel arrangement of capacitance $C_L$ and resistance $R_L$ is in series with capacitance $C_u$. This branch is mainly sensitive to changes in electrical properties of polymeric layer 25.

When the interacting fields are originating from the free surface of the piezoelectric crystal and are associated with the propagating acoustic wave (for example in a surface acoustic wave device), this interaction is often referred to an acousto-electric interaction. With the modified-electrode quartz crystal resonance device, the interacting fields consist of fringing fields originating from the edge of the electrode fringing fields and fields originating from a free surface (surface of the partially electroded region) of the crystal resonator device (due to the piezoelectric property of the quartz crystal). In the case of quartz, a weak piezoelectric material, the field originated from the free surface and associated with the acoustic wave is negligible. Therefore, the interacting fields are mainly due to the fringing fields. However, the interaction effects both the parallel and series resonances frequencies of the device through the loading process. The parallel resonance frequencies determined by the static capacitance, which is also effected by the electrical properties of the loading on the quartz crystal resonator and the mechanical properties of the quartz crystal resonator device. The parallel resonant frequency occurs at a frequency where the electrostatic capacitance parallel-resonates with the motional inductance. This can be seen as an external electrical load on the crystal which ideally does not, or should not, effect the crystal vibration. However, because the change of mass density associated with that load, the crystal mechanical vibration is also effected. Note that the series resonance frequency is a function of the mechanical properties of the quartz crystal resonator device and the mechanical properties of the load. As a result, the interaction between the electrical fields and charges (ions, electrons, and dipole) in the contacting medium is related to the antiresonance frequencies of the acoustic wave device. Therefore, this interaction is referred to here as an acousto-electric interaction.

Many coatings exist which can be used as the binding film of specific molecules or a class of molecules. In the present invention, the selectivity and specificity can optionally be enhanced by functionalizing the polymer for affinity to the target species. According to the present invention, detection occurs when the molecules are absorbed at the polymer surface, diffuse through the polymer or bind the polymer molecules. The result of this reaction can take the form of a change in the electrical properties of the layer, i.e., a change in the electrical conductivity and dielectric constant of the layer. In addition to measuring the change in the mass of the layer, by monitoring the critical frequencies of the exposed coated QCR or its impedance, the concentration of the target molecules can be measured.

By analyzing the equivalent circuit of the coated and exposed QCR in the narrow range of frequencies near resonance and antiresonance, the various critical frequencies can be defined. Furthermore, their variations as the electrical properties of the exposed layer as well as the mechanical properties change can be understood. FIG. 17 shows the equivalent circuit of a typical uncoated QCR with two identical electrodes. FIG. 16 shows the equivalent circuit of the polymer-coated QCR utilized in the present invention. In FIGS. 16 and 17, $C_o$ is the electrostatic capacitance arising from the two electrodes separated by the insulating quartz and is a function of the electrode size, shape and configuration. Since quartz is piezoelectric, the electromechanical coupling gives rise to the motional arm branch ($R_q$, $L_q$, $C_q$) in parallel with $C_o$. The motional resistance $R_m$ represents the mechanical dissipation of the QCR. In FIG. 16, $R_m$, $L_m$, and $C_m$ represent the mechanical loading of the chemically reactive polymer layer due to the viscosity, elastic constant and mass density, respectively. The electrical loading of the layer (or exposed layer) is represented by the capacitance $C_L$ and resistance $R_L$, and are due to the dielectric constant and conductivity, respectively. The capacitance, $C_u$, arises from the fields across the quartz plate between the lower electrode and the upper unelectroded interface (see FIGS. 1 through 3). Note that for a pure capacitive loading (pure dielectric layer), the series combination of $C_u$ and $C_L$, represents, a model of a partially filed parallel plate capacitor with a dielectric (quartz, $\epsilon_s$) on the lower plate, ant a dielectric $\epsilon_L$ (layer) between the quartz and the upper plate.

Figure 18:
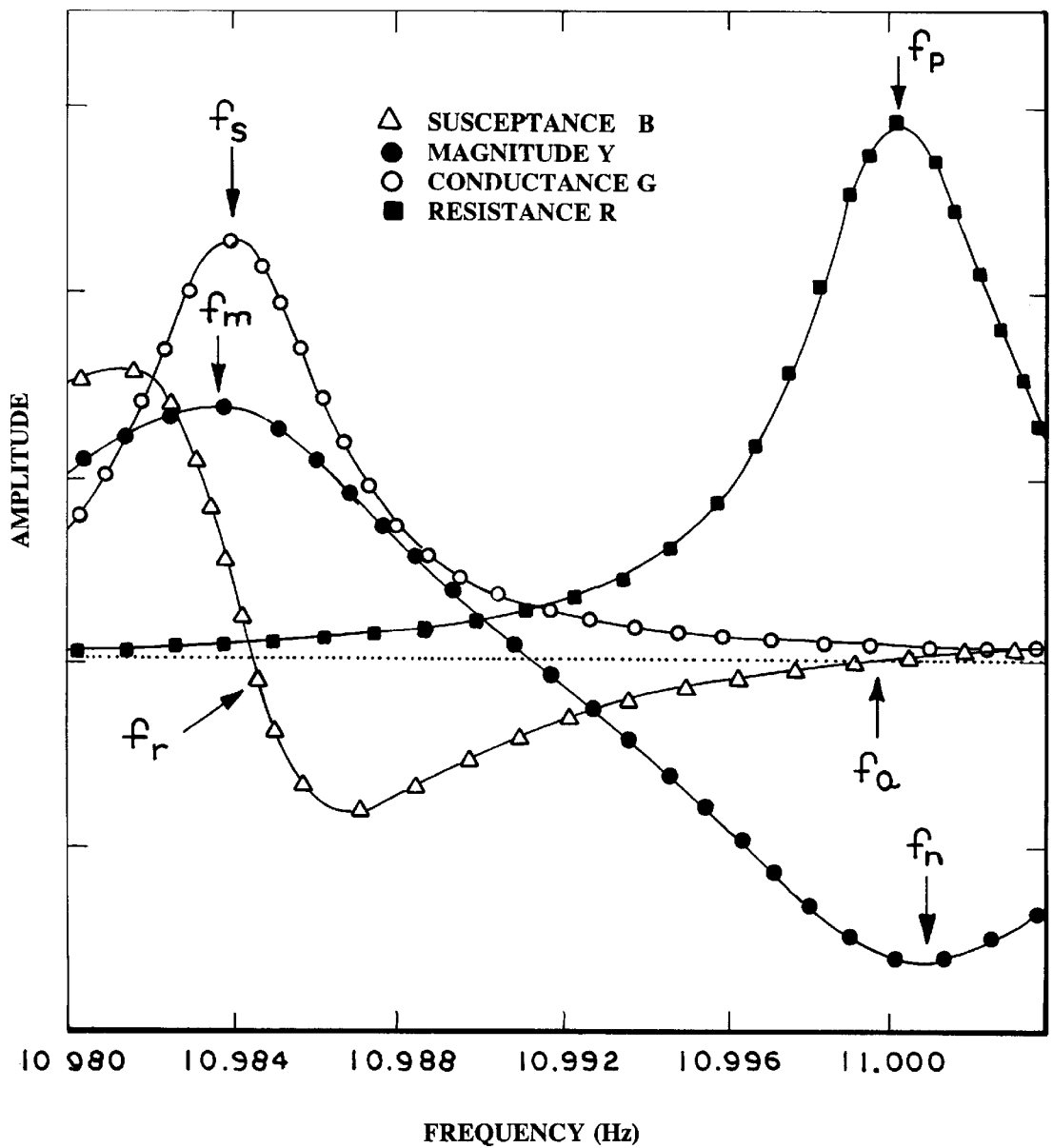
FIG. 18 shows measured impedance/admittance curves for the piezoelectric resonator sensor shown in FIG. 1 loaded with deionized water. Susceptance, conductance, resistance, and admitance are shown in the frequency domain.

For ideal lossless materials, in which the QCR impedance is purely reactive (R=O), only two critical frequencies ($f_1$ and $f_2$) are defined. The lower critical frequencies $f_1$ is defined as the frequency of maximum admittance. The upper critical frequency $f_2$ is defined as the frequency of maximum impedance. However, for lossy QCRs made from real materials (R≠O) or loads from lossy materials, there are two mechanisms of energy dissipation. The internal energy dissipation, $R_q$, results from the conversion of electrical energy into heat through friction. The external energy dissipation, $R_m$ results from the flow of electrical energy out of the QCR into the adjacent medium in the form of acoustic waves. Such energy dissipation mechanisms obscure the definition of $f_1$ and $f_2$ Thus, for a lossy QCR, such as a QCR loaded with a chemically reactive polymer exposed to a fluid, $f_1$ and $f_2$ are classified into two groups of closely spaced resonance frequencies ($f_m$, $f_s$, $f_r$) and antiresonance frequencies ($f_a$, $f_p$, $f_n$), respectively These represent six critical frequencies which can be used to characterize a lossy QCR. $f_m$ is the frequency of maximum admittance, $f_s$, is the series resonant frequency and $f_r$ is the resonant frequency. In the second group, $f_a$, $f_p$, and $f_n$, are the frequency of minimum admittance, the parallel resonant frequency and the antiresonant frequency, respectively. These frequencies can be easily extracted from the impedance/admittance characteristics of the loaded QCR (FIG. 18).

In particular, the antiresonant frequency group, $f_a$, $f_p$, and $f_n$ can be used to characterize the electrical properties of the layer and any subsequent change as a chemical reaction occurs. Moreover, each frequency in that group exhibits a different rate of variation. The operation of the QCR with modified-electrode coated with the chemically reactive polymer layer can be summarized as follows:

As the electrical properties (conductivity and dielectric constant) of the layer change, the overall electrostatic capacitance, $C_x$, of the loaded QCR changes and tends to that of a QCR with identical electrodes, i.e., $C_o$ of radius $r_2$. The relative change in $C_x$ is larger and the effects of changes in $C_x$ when the QCR is operated in antiresonant modes are no longer insignificant. Note that $C_x$ is a lossy capacitor.

Moreover, the series resonant frequency, $f_s$, invariant with changes in the electrical loading and function of the changes in the mass of the layer, can still be utilized as an additional measurement parameter. The chemical sensor apparatus includes a cell (or a chamber) to confine the gas (or liquid) to be measured to the coated surface, desirably a plurality of QCR devices such as those described in FIGS. 1 through 3 and the associated measurement electronics. Each device consists of a piezoelectric substrate, with dissimilar electrodes (FIGS. 1 through 3), one surface of which is coated with a functionalized polymer, desirably a different polymer for each device.

For ideal lossless materials, the impedance of the piezoelectric resonator is purely reactive (resistance equals zero) and only two critical frequencies are present. The two frequencies are the frequency of maximum admittance and the frequency of maximum impedance (minimum admittance).

However, as described herein in the model equivalent circuit (FIG. 16), there are two mechanisms dissipating energy in real piezoelectric materials. There is internal energy dissipation due to internal resistance $R_q$ and external energy dissipation due to resistance $R_m$.

Therefore, for a lossy piezoelectric resonator, such as piezoelectric resonator 10 in FIG. 1 having polymeric layer 25 exposed to fluid, the two frequencies listed above diverge into a first group of three closely spaced resonant frequencies and a second group of three closely spaced antiresonant frequencies.

The three resonant frequencies comprise the series resonant frequency $f_s$ (frequency of maximum conductance), the frequency of maximum admittance $f_m$ and the resonant frequency $f_r$. These three frequencies are close in value. $f_m$ is a lower frequency than $f_s$, and $f_s$ is a lower frequency than $f_r$.

The three antiresonant frequencies comprise the parallel resonant frequency $f_p$, the antiresonant frequency $f_a$, and the frequency of minimum admittance $f_n$. These three frequencies are close in value and greater than the resonant frequencies. $f_a$ is a lower frequency than $f_p$, and $f_p$ is a lower frequency than $f_n$.

These six critical frequencies can be used to characterize a lossy piezoelectric resonator unit 105. These frequencies can be extracted from impedance/admittance characteristics of piezoelectric resonator unit 105.

One method of calculating the six critical frequencies is as follows. The first step is calculating the capacitance $C_x$ of the third branch of the model equivalent circuit shown in FIG. 16. The capacitance $C_x$ is given by the equation:

$$C_x = \frac{C_u[G_L^2 + w^2 \cdot C_L(C_L + C_u)]}{G_L^2 + w^2 \cdot C_L(C_L + C_u)^2}$$

where $G_L$ equals $1/R_L$ and w equals the angular frequency of resonator unit 105.

The series resonant frequency $f_s$ does not vary with changes in the electrical loading of polymeric layer 25. Therefore, the calculated capacitance $C_x$ is not a factor in determining series resonant frequency $f_s$. Rather series resonant frequency $f_s$ changes in response to changes in the mass of polymeric layer 25. Series resonant frequency $f_s$ is the frequency of maximum conductance (i.e. minimum impedance), and is defined be the equation:

$$f_s = \frac{[(L_q + L_m)C_q]^{-1/2}}{2\pi}$$

where $L_q$, $L_m$, and $C_q$ are described earlier with reference to the model circuit.

Resonant frequency $f_r$ occurs when the imaginary part of the impedance of the piezoelectric resonator is zero. The resonant frequency $f_r$ is defined by the equation:

$$f_r = f_s(1 + r/2Q^2)$$

where r is defined by the equation:

$$r = (C_o + C_x)/C_q$$

and, where Q is the mechanical quality factor of the loaded piezoelectric resonator and defined by the equation:

$$Q = w\frac{(L_q + L_m)}{(R_q + R_m)}$$

The frequency of maximum admittance $f_m$ occurs when piezoelectric resonator 105 has maximum admittance (minimum impedance). The frequency of maximum admittance $f_m$ is defined by the equation:

$$f_m = f_s(1 - r/2Q^2)$$

where r and Q are as defined previously.

The three antiresonant frequencies are defined by equations as follows.

Parallel resonant frequency $f_p$ comprises the frequency where impedance is maximum, and is defined by the equation:

$$f_p = f_s(1 + \tfrac{1}{2}r)$$

Antiresonant frequency $f_a$ occurs when the imaginary part of the admittance is zero. Antiresonant frequency $f_a$ is defined by the following equation:

$$f_a = f_s(1 + \tfrac{1}{2}r - r/2Q^2)$$

The frequency of minimum admittance $f_n$ is defined by the following equation:

$$f_n = f_s(1 + \tfrac{1}{2}r + r/2Q^2)$$

As shown above, the six frequencies of interest are related to the electrical and mechanical properties of piezoelectric resonator unit 105. In particular, the antiresonant frequency group can be used to characterize the electrical properties of polymeric layer 25 and any subsequent change from sensing one or more materials in the medium.

Importantly, each antiresonant frequency $f_n$, $f_p$, and $f_a$ has a different rate of variation due to changes in the electrical properties of polymeric layer 25. FIG. 19 shows the shifting of antiresonant frequencies $f_n$, $f_p$, and $f_a$ with respect to changes in conductivity (Siemens/meter or 1/(ohm-meter)) of polymeric layer 25. Variations between the rates of change for each antiresonant frequency correlate with changes in the respective electrical properties of polymeric layer 25.

Further, series resonant frequency $f_s$ varies in response to mass loading on polymeric layer 25. Therefore, changes in one or more of the respective antiresonant frequencies and changes in the series resonant frequency can be correlated to detect the presence and concentration of one or more selected materials contacting polymeric layer 25.

In the present invention, both sensitivity and selectivity are enhanced. Sensitivity is enhanced by targeting, for example, a change in conductivity and/or dielectric constant of the layer. By measuring the antiresonant frequencies, $f_n$, $f_p$ and $f_a$ in addition to the commonly used series resonant frequency, $f_s$, with each frequency having a different rate of variation, selectivity is enhance with the increased number of measuring parameters.

The present invention also includes an apparatus containing multiple piezoelectric resonator units. Examples of this type of apparatus are shown in Examples 3 and 6 hereinbelow. The multiple piezoelectric resonator units can detect either the same analyte or several analytes, each unit detecting and measuring a different analyte.

This invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention.

EXAMPLE 1

FIG. 10 shows a basic embodiment of the invention including piezoelectric resonator unit 105, a source of electric energy desirably comprising an electronic circuit 100, a sensing circuit 115 and an indicator unit 120.

Oscillator circuit 100 drives piezoelectric resonator unit 105 by applying an electric signal of varying frequency over a range spanning all resonant and antiresonant frequencies. There are a large number of commercially available oscillator circuits capable of applying such an electric signal. For instance, FIG. 10 of U.S. Pat. No. 5,455,475, previously incorporated by reference, illustrates a tuned output oscillator circuit. This oscillator circuit is tuned by a suitable adjustment device. Those skilled in the art will understand that there are a variety of suitable oscillator circuits and that this is merely one exemplary circuit. Oscillator circuit 100 can sweep a narrow band of frequencies near series resonant frequency $f_s$. For example, the frequencies swept can be between 11.00 MHz and 11.01 MHz for a piezoelectric resonator unit having a series resonant frequency of about 11.005 MHz. This narrow range of frequencies can contain all six respective resonant and antiresonant frequencies.

Sensing circuit 110 can sweep a narrow band of frequencies containing the critical frequencies. Sensing circuit 110 measures or senses values of the resonant frequencies and respective magnitudes and/or phases of the impedances over the frequency range. Sensing circuit 110 also measures or senses the magnitude and/or phase of the admittance over the frequency range, and thereby determines the antiresonant critical frequencies.

Sensing circuit 110 correlates the sensed critical frequencies and respectively characterizes the electro-acoustic effect of the interaction of the medium with polymeric layer 25 (See, for example, FIG. 1). The sensed frequencies indicate changes in mass, conductivity, viscosity and dielectric constant of polymeric layer 25. These changes in properties of polymeric layer 25 can indicate the presence of one or more material of interest. The particular materials may bind, diffuse, absorb, adsorb, and/or chemically react with, or otherwise become temporarily or permanently attached to, polymeric layer 25, thereby changing electrical and mechanical properties of polymeric layer 25. A variety of analog or digital circuits, such as an electrical frequency counter, can act as sensing circuit 110.

Sensing circuit 110 desirably includes a computer 115. Computer 115 compares at least one resonant frequency and at least one antiresonant frequency (desirably at least two antiresonant frequencies) to determine changes in properties of polymeric layer 25 caused by one or more materials. Differences in the frequency values indicate the presence of one or more selected materials within the sample medium which interfaces with polymeric layer 25. Presence of such materials generally means presence either in polymeric layer 25 or at the interface between polymeric layer 25 and the sample medium.

Computer 115 can also compare the sensed critical frequencies with stored reference frequencies. The differences or similarities between selected stored frequencies and sensed critical frequencies, indicate the presence of one or more selected materials, or a class of materials. The stored frequencies can be earlier measured reference frequency values from piezoelectric resonator unit 105 or predetermined, calculated frequency values.

The selected materials can comprise selected molecules, molecule fragments, ions, or other moieties, in a gas or liquid medium. The selected one or more materials can comprise a class of materials such as halogenated hydrocarbons, (e.g.) chlorinated hydrocarbons.

An indicator unit 120 displays results from the computer. Indicator unit 120 indicates the presence or absence of one or more selected materials. The indicator can comprise a liquid crystal display, cathode ray tube, light emitting diode display, audio messages of the material sensed and its concentration, or the like.

Using series resonant frequency $f_s$, sensing circuit 115 can also measure the concentration of one or more materials. The concentration can be present in a gas or liquid medium adjacent polymeric layer 25. While FIG. 10 shows sensing circuit 115 and oscillator circuit 100 as separate elements, they may comprise a single unit or circuit.

In operation, oscillator circuit 100 oscillates resonator unit 105 at frequencies about its series resonant or parallel frequency. If one or more selected materials are present in the medium adjacent the outer surface of polymeric layer 25, changes in the mechanical loading and electrical properties of the polymeric layer can occur. These changes are caused by the materials of interest attaching to, reacting with, or otherwise associating with, the polymeric layer. These changes cause the critical resonant and anti-resonant frequencies to vary, as described earlier. Sensing circuit 110 senses at least one resonant frequency and at least one antiresonant frequency. Sensing circuit 110, desirably in combination with computer 115, then compares the sensed frequencies with reference frequencies to indicate the presence or absence of one or more materials of interest. The concentration is determined from the change in mass and electrical properties of polymeric layer 25. Indicator unit 120 then provides an indication of the material of interest, and its concentration.

EXAMPLE 2

Reference resonator unit

FIG. 11 shows an embodiment of the invention including a reference piezoelectric resonator unit 107. Oscillator circuit 100 provides electrical energy to first piezoelectric resonator unit 105 and second reference piezoelectric resonator unit 107. Sensing circuit 110 senses critical frequencies of both piezoelectric resonator units 105 and 107. Comparison circuit 125 compares the critical frequencies from both resonator units 105 and 107, and sends output signals to indicator unit 120.

Reference piezoelectric resonator unit 107 desirably comprises a unit substantially identical in electrode geometry and in the composition of polymeric layer 25 to piezoelectric resonator unit 105. Reference resonator unit 107 is closed or sealed from the medium (liquid or gas) that reaches piezoelectric resonator unit 105. Reference piezoelectric resonator unit 107 desirably is contained within a reference medium similar to the type of medium in which the material of interest is being carried.

Reference piezoelectric resonator unit 107 and first piezoelectric resonator unit 105 can be located in the same housing 109 or different housings. Desirably, the resonator units are in one housing 109.

Sensing circuit 110 senses two or more of the six critical frequencies. These frequencies vary according to changes in electrical and mechanical properties of polymeric layer 25 caused by one or more materials in the medium surrounding piezoelectric resonator unit 105.

Comparison circuit 125 compares selected respective frequencies of the first and second piezoelectric resonator units 105 and 107. Comparison circuit 125 can comprise analog or digital circuitry. A computer, as described earlier, can also perform such comparisons.

Indicator unit 120 displays results from comparison circuit 125. The results indicate the presence or absence of one or more selected materials in the medium at piezoelectric resonator unit 105. Indicator unit 120 can comprise a liquid crystal display, a light emitting diode display, and/or audio messages with the name of the material sensed. Indicator unit 120 can also display the concentration of the material sensed, if calculated by the computer.

According to this embodiment, reference resonator unit 107 provides a dynamic standard, subjected to all the same conditions as resonator unit 105, except the material of interest. Thus, differences between data collected simultaneously from units 105 and 107 represent influences of the material of interest, and reduced likelihood of extraneous other sources.

EXAMPLE 3

Plurality of resonator units

FIG. 12 shows another embodiment of the invention including an array of at least first and second piezoelectric resonator units 105 (four shown) in a single housing 109. Oscillator circuit 100 powers each respective piezoelectric resonator unit 105. The frequency of each piezoelectric resonator unit 105 is sensed by an electrical sensing circuit 110 Sensing circuit 110 senses at least two of the six critical frequencies generated by each of at least two of the respective piezoelectric resonator units.

The sensed frequencies from piezoelectric resonator units 105 are then correlated and compared with other respective critical or otherwise known or expected frequencies. Sensing circuit 110 desirably includes computer 115.

Computer 115 compares the sensed frequencies from the resonator units. A comparison of sensed frequency data indicates the presence of one or more materials of interest in the medium. The frequency data can also indicate the quantity of the one or more materials of interest in the medium adjacent polymeric layer 25.

In some embodiments, the geometries and/or surface areas of the electrodes differ (See, for example, electrodes 20 and 30 in FIG. 1). According to the present invention, the geometry of the first electrode 20 differs from electrode 30. The variations affect the critical frequencies in a predictable way. The variations in electrode structure can increase the sensitivity of the resonator unit 10, the ability to sense a variety of materials of interest and the ability to determine concentration of one or more materials of interest. Thus, the array of resonator units provides versatility in sensing, and processing through a single controller 115, a plurality of materials of interest, at a variety of concentrations, with varied degrees of sensitivity. To the extent the resonator units 105 are spaced from each other, the above properties can be detected and discriminated over the physical area represented by the spacing of the array.

In another embodiment, plural piezoelectric resonator units 105 are designed to resonate at different frequencies, such as 6, 9 and 11 MHz, to sense a variety of materials of interest. Desirably three or more different oscillator circuits 100 generate the respective different resonating frequencies. These different oscillator frequencies create differences in the frequency values sensed, i.e. the change in frequency sensed for respective piezoelectric resonator units 105. The frequencies generated by the piezoelectric resonator units can be correlated by computer 115 or an analog circuit. Indicator unit 120 then signals the presence of one or more selected materials and the concentration thereof based on the sensed data.

In yet another embodiment, the surface area and/or thickness of respective polymeric sensing layers 25 on each piezoelectric resonator 10 can be varied. The composition of polymeric sensing layer 25 can also be varied among the individual resonators 10. Particular sensing layers responsive to particular classes of materials, such as chlorinated hydrocarbons, can be segregated among the arrays. Polymeric layers 25 sensitive to specific materials are used to sense specific ones of those materials.

In operation, the piezoelectric resonator units 105 each have six critical frequencies by which the units 105 indicate changes in their respective polymeric layers 25. The numeric value of each frequency at a given time, of course, depends on the electrical, chemical, and mechanical conditions to which the respective resonator units 105 are subjected at the time within which the frequency data are recorded. These six frequencies are correlated and compared, desirably by computer 115. The computer compares the sensed frequencies from multiple resonator units 105 with each other. Further, if need be, computer 115 can compare the measured frequencies with data permanently stored in the computer corresponding to various groups of material. Such data comparison is used to indicate the presence and optionally concentration of particular materials. Multiple arrays of piezoelectric resonator units 105 can have different specific polymeric layers 25 responsive to the presence of different selected materials in the medium.

Of course, the surface area and size of the electrodes, the surface area and/or thickness as well as composition of polymeric layer 25, and the natural resonant frequency which depends on the size, shape and smoothness of piezoelectric resonator 10 can be varied in some or all of plural piezoelectric resonator units 105 in order to vary the sensitivity and/or responsiveness of the device. Thus, these variables can be manipulated to provide unique differences between and among the resonator units 105.

Further, varying active moieties of respective polymeric sensing layers 25 varies the sensitivity of the individual piezoelectric resonator units 105 with respect to each other. In this way, a variety of specific materials can be sensed.

Using combinations of the variations listed above, and other obvious variations, increases the selectivity to specific materials, and the accuracy in measuring concentrations of such materials.

Indicator unit 120, as described earlier, then displays information related to the presence of one or more sensed materials, including, for example, concentrations of such materials.

Although a single housing 109 contains arrays of resonator units 1–4, multiple housings for one or more resonator units are also contemplated. Piezoelectric resonator units 105 are structured, and associated medium containment environments are arranged, so that the medium contacts the side of piezoelectric resonator 105 at polymeric layer 25, and does not contact the opposite side of piezoelectric resonator 10 (e.g. at electrode 30).

EXAMPLE 4

Resonator units having "effective" electrodes

Another embodiment of the invention includes piezoelectric resonator 10, desirably without a polymeric sensing layer 25. This embodiment can be considered within the context of the basic block diagram of FIG. 10. This apparatus includes first and second electrodes 20 and 30 as described earlier (See FIG. 1, 2 or 3), a piezoelectric resonator 10, and an oscillator circuit 100 providing energy, but is devoid of polymeric layer 25, per se.

In operation, the apparatus senses when the medium contacting the first side of piezoelectric resonator 105 has sufficient conductivity change and an initial mass to alter the series resonant frequency. The conductive medium forms an effective temporary electrode including first electrode 20 and the conductive medium on the first side of the piezoelectric resonator. By an effective electrode, it is meant that the conductive medium, for example, a liquid has an effect corresponding to a conductor coating the entire first side of piezoelectric resonator 105. Thus, as the medium establishes contact with the piezoelectric resonator 10 and first electrode 20, the first electrode's surface area effectively increases to include all of the surface area of resonator 10 and electrode 20 contacted by the medium, thus changing the series resonant frequency of piezoelectric resonator 105 (energy trapping phenomenon). When the medium is withdrawn from contact with resonator 10 and electrode 20, the "effective" electrode characteristics also depart the sensor.

The change in size of the "effective" electrode changes the response of series resonant frequency $f_s$. This change in frequency is not dependent upon the mass loading of piezoelectric resonator 10 but rather dependent on the so-called electrode mass loading factor. The electrode mass loading factor changes the acoustic wave particle displacement amplitude profile (energy trapping). This signal provides an indication of the presence of a conductive medium.

Indicator unit 120 provides a yes/no type indication of the conductivity of the medium.

EXAMPLE 5

Sensor with a gradient polymeric layer

FIG. 13 shows a top view of another embodiment of piezoelectric resonator units 10 of the invention. In this embodiment, polymeric layer 25 is a composite of two or more zones of two or more different polymeric materials. Polymeric zone 11 has a relatively pure composition of e.g. polymer A. Similarly, polymer zone 25 has a relatively pure composition of e.g. polymer B. Central polymeric zone 13 comprises a combination of polymers A and B, generally graduated in its composition according to its distance from zones 11 and 12. Portions of the area covered by zones 11, 12 and 13 is desirably underlaid by electrode 10 as shown in FIG. 14.

The gradient arrangement as at zone 13 can be formed as set forth in "Molecular Gradients of -Substituted Alkanethiols on Gold: Preparation and Characterization", by Bo Liedberg and Pentti Tengvall, published in Langmuir, Vol. 11, No. 10, 1995, pp. 3821–3827, hereby incorporated by reference. As taught therein, central zone 13 represents a gradually changing interfacial region that comprises a concentration gradient between two adjacent phases. This gradient desirably is formed by a cross-diffusion method. This method enables two or more precursors of polymeric layer 25 to diffuse and intermix, such as in a preformed matrix, and to simultaneously bond with gold electrodes during formation thereof.

Electrodes 20 and 30 are first formed on piezoelectric resonator 10. Desirably a layer of chromium is deposited first, followed by a layer of gold or other conductive material. The gold electrodes are cleaned in an ethanol solution. A diffusion matrix is formed on the gold electrodes. The diffusion matrix desirably comprises one part Sephadex LH-20 and three parts ethanol.

Porous glass filters or dams are then pressed into the matrix in spaced relationship as shown in FIG. 1 on page 3823 of the Liedberg et al publication. The Sephadex LH-20 then homogenizes while ethanol evaporates until a 5 millimeter thick diffusion matrix forms on electrode 20.

Two different polymers, such as thiol solutions, are then deposited on the two glass dams or filters to diffuse in the matrix as shown in FIG. 1 on page 3823 of the Liedberg et al publication. Over time, the two polymers move toward each other, and eventually diffuse into each other at zone 13 forming the graduated composite polymer. Central zone 13 contains more of the polymer composition of polymer zone 11 on the left side thereof, and more of the polymer composition of polymer zone 12 on the right side thereof as seen in FIG. 13. As one examines the concentrations across the composite polymer in central zone 13, the concentrations increase or decrease similar to the graphs set forth in FIG. 4 on page 3824 of the Liedberg et al publication.

FIG. 14 shows the relationship between electrodes 20, 30, polymer zones 11, 12 and central zone 13. Electrode 20, of course, can be varied as shown by the electrode in the embodiment of FIGS. 1 through 3.

The graduated composite polymeric layer 25 provides a broad range of blends of polymer compositions A and B, which can selectively respond to the presence or absence of materials of interest that neither polymer A nor polymer B respond to separately.

Further, as described earlier, each polymeric zone 11, 12 can include a separate and distinct moiety functionalized for sensing selected materials.

This embodiment of the invention can be utilized in any of the various arrangements discussed earlier or hereafter. Central zone 13 can thus increase the sensitivity of piezoelectric resonator unit 105 to selected materials present in a medium.

EXAMPLE 6

Filter embodiment

FIG. 15 shows filter 130 mounted in a fluid pipeline 135. Piezoelectric resonator units 105a and 105b are mounted upstream and downstream of filter 130. Arrows 140 illustrate the direction of fluid flow in the pipeline. Pipeline 135 desirably carries a fluid including materials, such as chlorinated hydrocarbons, whose presence is to be sensed. Oscillator circuit 100 powers both piezoelectric resonator units 105. Sensing circuit 110 senses at least two of the six critical frequency signals from piezoelectric resonator units 105. Sensing circuit 110 sends frequency signals to comparison circuit 125. Comparison circuit 125 compares the sensed critical frequencies and provides an output to indicator unit 120.

Filter 130 can comprise any well known type of filter. In a preferred embodiment, filter 130 comprises a charcoal filter which removes chlorinated hydrocarbons from water.

Piezoelectric resonator units 105a and 105b generally comprise one of the two specific units described earlier with respect to FIGS. 1 through 3. The resonator units may differ, one from the other, but desirably piezoelectric resonator units 105a and 105b are substantially identical to each other.

Comparison circuit 125 can comprise digital and/or analog circuitry. The comparison circuit can also utilize a computer, such as a microprocessor, referred to earlier as computer 115.

Indicator unit 120 desirably comprises a liquid crystal display, cathode ray tube display, light emitting diode array, or the like. Further, indicator unit 120 can include an audible alarm to draw attention to the failure or other end of use life of filter 135.

In operating the filter application shown in FIG. 15, comparison circuit 125 first determines the presence of a material of interest by sensing changes in critical frequencies from upstream piezoelectric resonator unit 105a. Filter 130 captures such material preventing further passage of such material through pipeline 135. Comparison unit 31 then compares frequencies from first piezoelectric resonator unit 105a with those of second downstream resonator unit 105b. As filter 130 approaches the end of its useful life, increasing concentrations of the material of interest pass through the filter, uncaptured. Respectively, piezoelectric resonator unit 105b senses and reports the dynamic changes in concentration of such material in the fluid downstream of filter 130. As the concentration reaches a critical level, such as when the signals are substantially the same, indicating failure or other end of life indicator for filter 130, a signal is sent to indicator unit 120. Indicator unit 120 then provides an indication of filter condition. In the alternative, indicator unit 120 can provide an ongoing indication of filter condition.

While the embodiment of FIG. 15 shows two piezoelectric resonator units 105a, 105b, a single downstream piezoelectric resonator unit can also be utilized to perform the same function. Piezoelectric resonator unit 105, for example, can sense the presence of a threshold value of chlorinated hydrocarbons. The critical frequencies sensed by sensor circuit 110 are then sent to comparison circuit 125. Comparison circuit 125, can compare the value of sensed frequencies with values of stored frequencies to indicate the presence of a selected material. Indicator unit 120 generates an alarm or indication in response to the presence of the selected material.

While all of the apparatus disclosed in this application relate to sensing and indicating the presence of one or more materials of interest, and the presence and/or concentration thereof, other uses are contemplated. For instance, indicator unit 120 can also control a shut-off valve, shut-down system or any other type of control device in response to the presence and/or concentration of one or more materials of interest.

Those skilled in the art will now see that certain modifications can be made to the invention herein disclosed with respect to the illustrated embodiments, without departing from the spirit of the instant invention. And while the invention has been described above with respect to the preferred embodiments, it will be understood that the invention is adapted to numerous rearrangements, modifications, and alterations, all such arrangements, modifications, and alterations are intended to be within the scope of the appended claims.

We claim:

1. A sensing device for measuring an analyte in a medium comprising:

a piezoelectric resonator having a first side and a second side, the first side having a first electrode thereon and the second side having a second electrode thereon wherein the first electrode has a different geometry than the second electrode whereby the sensing device has a group of resonant frequencies comprising a frequency of maximum admittance, a series resonant frequency and a resonant frequency and a group of antiresonant frequencies comprising a frequency of maximum admittance, a parallel resonant frequency and an antiresonant frequency;

a polymeric layer on the first side of the piezoelectric resonator, at least a portion of the polymeric layer being disposed on the electrode; and means for sensing at least one resonant frequency and at least one antiresonant frequency.

2. The sensing device of claim 1, wherein the first and second electrodes have a geometry which is generally circular, the first electrode circular geometry being smaller in diameter than the second electrode circular geometry.

3. The sensing device of claim 1, wherein the second electrode has a geometry which is generally circular and the first electrode has a geometry that is a ring.

4. The sensing device of claim 1, wherein the polymeric layer includes a moiety selective to the analyte.

5. The sensing device of claim 4, wherein the moiety selective to the analyte is selected from the group consisting of antibodies, fragments of antibodies, avidin, enzymes, biotin, and strep A protein.

6. The sensing device of claim 4, wherein the analyte is selected from the group consisting of proteins, glycoproteins, metal salts, ions, neurotransmitters, hormones, growth factors, cytokines, monokines, lymphokines, nutrients, enzymes, and receptors.

7. The sensing device of claim 1, wherein the polymeric layer comprises a material selected from the group consisting of poly(diphenylmethylsiloxanes), poly(etherurethanes), poly(epichlorohydrins) and poly(1,1,1-trifluoropropylmethylsiloxanes).

8. The sensing device of claim 1, wherein the device can sense an analyte selected from the group consisting of trichloromethane, tetrachloromethane, trichloroethane, trichloroethylene, tetrachloroethane, tetrachloroethylene and toluene.

9. An apparatus for measuring an analyte in a medium comprising:

a piezoelectric resonator having a first side, and a second opposing side;

a source of electric energy, providing an electric signal;

a first electrode on the first side of the piezoelectric resonator and a second electrode on the second side of the piezoelectric resonator, wherein the first electrode has a different geometry than the second electrode;

a polymeric layer on the first side of the piezoelectric resonator, at least a portion of the polymeric layer being partially disposed on the first electrode; and an electrical sensing circuit sensing at least one of a group of resonant frequencies comprising a frequency of maximum admittance, a series resonant frequency, and a resonant frequency and at least one of a group of antiresonant frequencies comprising a frequency of minimum admittance, a parallel resonant frequency, and an antiresonant frequency of the piezoelectric resonator.

10. The apparatus of claim 9, wherein said polymeric layer selectively attaches to, reacts with, or otherwise associates with the analyte.

11. The apparatus of claim 9, wherein the composition of said polymeric layer is selected from compositions functionally operable to provide a change in a resonant or anti-resonant frequency of said piezoelectric resonator in response to at least one of presence and concentration of the analyte at said polymer layer.

12. The apparatus of claim 9, wherein the polymeric layer covers the first electrode.

13. The apparatus of claim 9, wherein the polymeric layer is confined within a projected outline of the second electrode.

14. The apparatus of claim 9, wherein the polymeric layer includes a moiety selective to the analyte.

15. The apparatus of claim 9, wherein the polymeric layer comprises a material selected from the group consisting of poly(diphenylmethylsiloxanes), poly(etherurethanes), poly(epichlorohydrins) and poly(1,1,1-trifluoropropylmethylsiloxanes).

16. The apparatus of claim 9, wherein the device can sense an analyte selected from the group consisting of trichloromethane, tetrachloromethane, trichloroethane, trichloroethylene, tetrachloroethane, tetrachloroethylene and toluene.

17. The apparatus of claim 9, wherein said electrical sensing circuit senses at least two antiresonant frequencies.

18. The apparatus of claim 9, wherein said electrical sensing circuit sweeps frequencies in a band containing the respective resonant and antiresonant frequencies.

19. The apparatus of claim 9, further comprising:
a second reference piezoelectric resonator having a third side, and a fourth opposing side;
a third electrode on the third side of the second reference piezoelectric resonator and a fourth electrode on the fourth side of the second reference piezoelectric resonator, wherein the third electrode has a different geometry than the fourth electrode;
a second polymeric layer on the third side of said second reference piezoelectric resonator;
an electrical sensing circuit sensing at least one of a group of resonant frequencies comprising a frequency of maximum admittance, a series resonant frequency and a resonant frequency and at least one of a group of antiresonant frequencies comprising a frequency of minimum admittance, a parallel resonant frequency, and an antiresonant frequency of each of said first and second piezoelectric resonators; and
a comparison circuit comparing the respective resonant and anti-resonant frequencies of the first and second piezoelectric resonators.

20. A method of detecting or measuring an analyte in a medium comprising:
contacting the medium in which there is suspected to be an analyte with a piezoelectric resonator in an apparatus comprising:
(a) the piezoelectric resonator having a first side, and a second opposing side;
(b) a source of electric energy, providing an electric signal;
(c) a first electrode on the first side of the piezoelectric resonator and a second electrode on the second side of the piezoelectric resonator, wherein the first electrode has a different geometry than the second electrode;
(d) a polymeric layer on the first side of the piezoelectric resonator, at least a portion of the polymeric layer being partially disposed on the first electrode; and
(e) an electrical sensing circuit sensing at least one of a group of resonant frequencies comprising a frequency of maximum admittance, a series resonant frequency, and a resonant frequency and at least one of a group of antiresonant frequencies comprising a frequency of minimum admittance, a parallel resonant frequency, and an antiresonant frequency of the piezoelectric resonator; and
measuring the change in the at least one resonant frequency and the at least one antiresonant frequency and correlating the changes in the at least one resonant frequency and the at least one antiresonant frequency to the presence or amount of analyte in the medium.

21. The method of claim 20, wherein said polymeric layer selectively attaches to reacts with, or otherwise associates with the analyte.

22. The method of claim 20, wherein the composition of said polymeric layer is selected from compositions functionally operable to provide a change in a resonant or anti-resonant frequency of said piezoelectric resonator in response to at least one of presence and concentration of the material of interest at said polymer layer.

23. The method of claim 20, wherein the polymeric layer covers the first electrode.

24. The method of claim 20, wherein the polymeric layer is confined within a projected outline of the second electrode.

25. The method of claim 20, wherein the polymeric layer includes a moiety selective to the analyte.

26. The method of claim 20, wherein the polymeric layer comprises a material selected from the group consisting of poly(diphenylmethylsiloxanes), poly(etherurethanes), poly(epichlorohydrins) and poly(1,1,1-trifluoropropylmethylsiloxanes).

27. The method of claim 20, wherein the analyte is selected from the group consisting of trichloromethane, tetrachloromethane, trichloroethane, trichloroethylene, tetrachloroethane, tetrachloroethylene and toluene.

28. The method of claim 20, wherein said electrical sensing circuit senses at least two antiresonant frequencies.

29. The method of claim 20, wherein said electrical sensing circuit sweeps frequencies in a band containing the respective resonant and antiresonant frequencies.

* * * * *